(12) United States Patent
Sathyanarayanan et al.

(10) Patent No.: US 8,852,590 B2
(45) Date of Patent: Oct. 7, 2014

(54) COMPOSITIONS AND METHODS FOR TREATING CANCER

(75) Inventors: Sriram Sathyanarayanan, Natick, MA (US); Christopher Winter, Needham, MA (US); Richard Klinghoffer, Seattle, WA (US)

(73) Assignees: Merck Sharp & Dohme Corp., Rahway, NJ (US); Ariad Pharmaceuticals, Inc., Cambridge, MA (US)

( * ) Notice: Subject to any disclaimer, the term of this patent is extended or adjusted under 35 U.S.C. 154(b) by 107 days.

(21) Appl. No.: 13/264,060

(22) PCT Filed: Apr. 6, 2010

(86) PCT No.: PCT/US2010/030074
§ 371 (c)(1),
(2), (4) Date: Oct. 12, 2011

(87) PCT Pub. No.: WO2010/120599
PCT Pub. Date: Oct. 21, 2010

(65) Prior Publication Data
US 2012/0027757 A1    Feb. 2, 2012

Related U.S. Application Data

(60) Provisional application No. 61/169,757, filed on Apr. 16, 2009.

(51) Int. Cl.
*A61K 39/395* (2006.01)
*A61P 35/00* (2006.01)
*A61K 31/4353* (2006.01)

(52) U.S. Cl.
CPC .......... *A61K 31/4353* (2013.01); *A61K 39/395* (2013.01); *A61K 39/39541* (2013.01)
USPC .................................... 424/133.1; 424/142.1

(58) Field of Classification Search
None
See application file for complete search history.

(56) References Cited

U.S. PATENT DOCUMENTS

| | | | |
|---|---|---|---|
| 5,362,718 A | 11/1994 | Skotnicki et al. | |
| 5,665,772 A | 9/1997 | Cottens et al. | |
| 7,037,498 B2 | 5/2006 | Cohen et al. | |
| 7,091,213 B2 | 8/2006 | Metcalf, III et al. | |
| 7,217,796 B2 | 5/2007 | Wang et al. | |
| 7,241,444 B2 * | 7/2007 | Goetsch et al. | 424/130.1 |
| 7,378,503 B2 | 5/2008 | Graus et al. | |
| 7,538,195 B2 | 5/2009 | Singh et al. | |
| 7,553,485 B2 | 6/2009 | Goetsch et al. | |
| 7,638,605 B2 | 12/2009 | Ludwig | |
| 8,173,167 B2 * | 5/2012 | Kwon et al. | 424/489 |
| 8,496,967 B2 | 7/2013 | Vladyka, Jr. et al. | |
| 2005/0084906 A1 | 4/2005 | Goetsch et al. | |
| 2007/0185150 A1 | 8/2007 | Bedrosian | |
| 2008/0193445 A1 | 8/2008 | Goetsch et al. | |
| 2009/0068110 A1 | 3/2009 | Shang et al. | |
| 2009/0274698 A1 * | 11/2009 | Bhagwat et al. | 424/139.1 |

FOREIGN PATENT DOCUMENTS

| | | |
|---|---|---|
| WO | 03106621 A2 | 12/2003 |
| WO | 2006069202 A2 | 6/2006 |
| WO | 2009008992 A2 | 1/2009 |

OTHER PUBLICATIONS

NCT00610129 on Feb. 6, 2008: ClinicalTrials.gov Archive.*
NCT00654420 on Apr. 7, 2008: ClinicalTrials.gov Archive.*
Ridaforolimus, Jun. 2, 2010, http://en.wikipedia.org/wiki/Ridaforolimus, support data demonstrating aliases for ridaforolimus.
Clinical Trials Feeds, "Study of dalotuzumab (MK0646) in combination with cetuximab and irinotecan in metastatic colorectal cancer", May 6, 2010, http://clinicaltrialsfeeds.org/clinical-trials/show/NCT00614393.
Wan, X et al., Oncogene, (2007), vol. 26, pp. 1932-1940, "Rapamycin induces feedback activation of Akt signaling through an IGF-1R-dependent mechanism".
Bertrand, FE et al., Leukemia, (2006), vol. 20, pp. 1254-1260, "Synergy between an IGF-1R antibody and Raf/MEK/ERK and PI3K/Akt/mTOR pathway inhibitors in suppressing IGF-1R-mediated growth in hematopoietic cells".
O'Reilly, KE et al., Cancer Research (2006), vol. 66(3), pp. 1500-1508, "mTOR inhibition induces upstream receptor tyrosine kinase signaling and activates Akt".
Hewish, M et al., Recent Patents on Anti-Cancer Drug Discovery (2009), vol. 4, pp. 54-72, "Insulin-like growth factor 1 receptor targeted therapeutics: Novel compounds and novel treatment strategies for cancer medicine".
Sun, SY et al., Cancer Research (2005), vol. 65(16), pp. 7052-7058, "Activation of Akt and eIF4E survival pathways by rapamycin-mediated mammalian target of rapamycin inhibition".
Gardner, H et al., Breast Cancer Research and Treatment (2007), vol. 106 (Suppl 1), San Antonio Breast Cancer Symposium, San Antonio, TX, Dec. 13-16, 2007, Abstract 4006, "Biomarker analysis of a phase II double-blind randomized trial of daily oral RAD001 (everolimus) plus letrozole or placebo plus letrozole as neoadjuvant therapy for patients with estrogen receptor positive breast cancer".
Kurmasheva, RT et al., AACR-NCI-EORTC, International Conference: Molecular Targets and Cancer Therapeutics, Oct. 22-26, 2007, San Francisco, CA, Abstract C172, "Combination of CP-751871, a human monoclonal antibody agaInstitute the IGF-1 receptor, with rapamycin results in a highly effective therapy for xenografts derived from childhood sarcomas".
Darko, I et al., 98th AACR Annual Meeting, Apr. 14-18, 2007, Los Angeles, CA, Abstract 4760, "Evaluation of combined insulin-like growth factor receptor type I (IGF-1R) and mTOR pathway blockade in sarcoma xenograft models".
Kurmasheva, RT et al., Cancer Research (2009), vol. 69(19), pp. 7662-7671, "The insulin-like growth factor-1 receptor-targeting antibody, CP-751,871, suppresses tumor-derived VEGF and synergizes with rapamycin in models of childhood sarcoma".
Cao, L et al., Cancer Research (2008), vol. 68(19), pp. 8039-8048, "Addiction to elevated insulin-like growth factor I receptor and initial modulation of the AKT pathway define the responsiveness of rhabdomyosarcoma to the targeting antibody".

(Continued)

*Primary Examiner* — Marianne P Allen
(74) *Attorney, Agent, or Firm* — Li Su; Laura M. Ginkel

(57) ABSTRACT

A method of treating a cancer with an mTOR inhibitor and an anti-IGF-1 R antibody is disclosed.

1 Claim, 13 Drawing Sheets

(56) References Cited

OTHER PUBLICATIONS

Cloughesy, TF et al., PLOS Medicine, (2008), vol. 5(1), pp. 139-151, "Antitumor activity of rapamycin in a phase I trial for patients with recurrent PTEN-deficient glioblastoma".

Camidge, DR et al., Clinical Lung Cancer, vol. 10, No. 4, pp. 267-272 (2009), "The rationale and development of therapeutic insulin-like growth factor asix inhibition for lung and other cancers".

Sathyanarayanan S, et al., AACR Annual Meeting, Apr. 18-22, 2009, vol. 50, p. 679, Abstract 2809, (2009), "Combination treatment with the anti-IGF1R antibody MK-0646 and the mTOR inhibitor deforolimus leads to more effective P13K pathway targeting and anti-tumor activity".

Baumann, P et al., Anti-Cancer Drugs, vol. 20, No. 4, pp. 259-266, (2009), "Myeloma cell growth inhibition is augmented by synchronous inhibition of the insulin-like growth factor-1 receptor by NVP-AEW541 and inhibition of mammalian target of rapamycin by Rad001".

Kurmasheva, RT et al., AACR-NCI-EORTC International Conference, Abstract C172, p. 312, (2007) "Combination of CP-751871, a human monoclonal antibody against the IGF-1 receptor, with rapamycin results in a highly effective therapy for xenografts derived from childhood sarcomas".

\* cited by examiner

O'Reilly et al Cancer Res 2006

SEQUENCE LISTING

<160> NUMBER OF SEQ ID NOS: 13

<210> SEQ ID NO 1
<211> LENGTH: 16
<212> TYPE: PRT
<213> ORGANISM: Artificial Sequence
<220> FEATURE:
<223> OTHER INFORMATION: Completely synthetic amino acid

<400> SEQUENCE: 1

-continued

Arg Ser Ser Gln Ser Ile Val His Ser Asn Gly Asn Thr Tyr Leu Gln
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Completely synthetic amino acid

<400> SEQUENCE: 2

Lys Val Ser Asn Arg Leu Tyr
1               5

<210> SEQ ID NO 3
<211> LENGTH: 9
<212> TYPE: PRT
<213> ORGANISM: Artificial Sequence
<220> FEATURE:
<223> OTHER INFORMATION: Completely synthetic amino acid

<400> SEQUENCE: 3

Phe Gln Gly Ser His Val Pro Trp Thr
1               5

<210> SEQ ID NO 4
<211> LENGTH: 6
<212> TYPE: PRT
<213> ORGANISM: Artificial Sequence
<220> FEATURE:
<223> OTHER INFORMATION: Completely synthetic amino acid

<400> SEQUENCE: 4

Gly Gly Tyr Leu Trp Asn
1               5

<210> SEQ ID NO 5
<211> LENGTH: 16
<212> TYPE: PRT
<213> ORGANISM: Artificial Sequence
<220> FEATURE:
<223> OTHER INFORMATION: Completely synthetic amino acid

<400> SEQUENCE: 5

Tyr Ile Ser Tyr Asp Gly Thr Asn Asn Tyr Lys Pro Ser Leu Lys Asp
1               5                   10                  15

<210> SEQ ID NO 6
<211> LENGTH: 8
<212> TYPE: PRT
<213> ORGANISM: Artificial Sequence
<220> FEATURE:
<223> OTHER INFORMATION: Completely synthetic amino acid

<400> SEQUENCE: 6

Tyr Gly Arg Val Phe Phe Asp Tyr
1               5

<210> SEQ ID NO 7
<211> LENGTH: 112
<212> TYPE: PRT
<213> ORGANISM: Artificial Sequence
<220> FEATURE:
<223> OTHER INFORMATION: Completely synthetic amino acid

<400> SEQUENCE: 7

Asp Val Val Met Thr Gln Ser Pro Leu Ser Leu Pro Val Thr Pro Gly

```
                1               5                  10                 15
        Glu Pro Ala Ser Ile Ser Cys Arg Ser Ser Gln Ser Ile Val His Ser
                        20                  25                  30

Asn Gly Asn Thr Tyr Leu Gln Trp Tyr Leu Gln Lys Pro Gly Gln Ser
                    35                  40                  45

Pro Gln Leu Leu Ile Tyr Lys Val Ser Asn Arg Leu Tyr Gly Val Pro
                50                  55                  60

Asp Arg Phe Ser Gly Ser Gly Ser Gly Thr Asp Phe Thr Leu Lys Ile
        65                  70                  75                  80

Ser Arg Val Glu Ala Glu Asp Val Gly Val Tyr Tyr Cys Phe Gln Gly
                        85                  90                  95

Ser His Val Pro Trp Thr Phe Gly Gln Gly Thr Lys Val Glu Ile Lys
                    100                 105                 110
```

<210> SEQ ID NO 8
<211> LENGTH: 112
<212> TYPE: PRT
<213> ORGANISM: Artificial Sequence
<220> FEATURE:
<223> OTHER INFORMATION: Completely synthetic amino acid

<400> SEQUENCE: 8

```
        Asp Ile Val Met Thr Gln Ser Pro Leu Ser Leu Pro Val Thr Pro Gly
        1               5                   10                  15

Glu Pro Ala Ser Ile Ser Cys Arg Ser Ser Gln Ser Ile Val His Ser
                        20                  25                  30

Asn Gly Asn Thr Tyr Leu Gln Trp Tyr Leu Gln Lys Pro Gly Gln Ser
                    35                  40                  45

Pro Gln Leu Leu Ile Tyr Lys Val Ser Asn Arg Leu Tyr Gly Val Pro
                50                  55                  60

Asp Arg Phe Ser Gly Ser Gly Ser Gly Thr Asp Phe Thr Leu Lys Ile
        65                  70                  75                  80

Ser Arg Val Glu Ala Glu Asp Val Gly Val Tyr Tyr Cys Phe Gln Gly
                        85                  90                  95

Ser His Val Pro Trp Thr Phe Gly Gln Gly Thr Lys Val Glu Ile Lys
                    100                 105                 110
```

<210> SEQ ID NO 9
<211> LENGTH: 117
<212> TYPE: PRT
<213> ORGANISM: Artificial Sequence
<220> FEATURE:
<223> OTHER INFORMATION: Completely synthetic amino acid

<400> SEQUENCE: 9

```
        Gln Val Gln Leu Gln Glu Ser Gly Pro Gly Leu Val Lys Pro Ser Glu
        1               5                   10                  15

Thr Leu Ser Leu Thr Cys Thr Val Ser Gly Tyr Ser Ile Thr Gly Gly
                        20                  25                  30

Tyr Leu Trp Asn Trp Ile Arg Gln Pro Pro Gly Lys Gly Leu Glu Trp
                    35                  40                  45

Met Gly Tyr Ile Ser Tyr Asp Gly Thr Asn Asn Tyr Lys Pro Ser Leu
                50                  55                  60

Lys Asp Arg Ile Thr Ile Ser Arg Asp Thr Ser Lys Asn Gln Phe Ser
        65                  70                  75                  80

Leu Lys Leu Ser Ser Val Thr Ala Ala Asp Thr Ala Val Tyr Tyr Cys
                        85                  90                  95
```

```
Ala Arg Tyr Gly Arg Val Phe Phe Asp Tyr Trp Gly Gln Gly Thr Leu
                100                 105                 110

Val Thr Val Ser Ser
        115

<210> SEQ ID NO 10
<211> LENGTH: 117
<212> TYPE: PRT
<213> ORGANISM: Artificial Sequence
<220> FEATURE:
<223> OTHER INFORMATION: Completely synthetic amino acid

<400> SEQUENCE: 10

Gln Val Gln Leu Gln Glu Ser Gly Pro Gly Leu Val Lys Pro Ser Glu
  1               5                  10                  15

Thr Leu Ser Leu Thr Cys Thr Val Ser Gly Tyr Ser Ile Thr Gly Gly
             20                  25                  30

Tyr Leu Trp Asn Trp Ile Arg Gln Pro Pro Gly Lys Gly Leu Glu Trp
         35                  40                  45

Ile Gly Tyr Ile Ser Tyr Asp Gly Thr Asn Asn Tyr Lys Pro Ser Leu
 50                  55                  60

Lys Asp Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Tyr Gly Arg Val Phe Phe Asp Tyr Trp Gly Gln Gly Thr Leu
                100                 105                 110

Val Thr Val Ser Ser
        115

<210> SEQ ID NO 11
<211> LENGTH: 117
<212> TYPE: PRT
<213> ORGANISM: Artificial Sequence
<220> FEATURE:
<223> OTHER INFORMATION: Completely synthetic amino acid

<400> SEQUENCE: 11

Gln Val Gln Leu Gln Glu Ser Gly Pro Gly Leu Val Lys Pro Ser Glu
  1               5                  10                  15

Thr Leu Ser Leu Thr Cys Thr Val Ser Gly Tyr Ser Ile Ser Gly Gly
             20                  25                  30

Tyr Leu Trp Asn Trp Ile Arg Gln Pro Pro Gly Lys Gly Leu Glu Trp
         35                  40                  45

Ile Gly Tyr Ile Ser Tyr Asp Gly Thr Asn Asn Tyr Lys Pro Ser Leu
 50                  55                  60

Lys Asp Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Tyr Gly Arg Val Phe Phe Asp Tyr Trp Gly Gln Gly Thr Leu
                100                 105                 110

Val Thr Val Ser Ser
        115

<210> SEQ ID NO 12
<211> LENGTH: 112
<212> TYPE: PRT
<213> ORGANISM: Artificial Sequence
```

```
<220> FEATURE:
<223> OTHER INFORMATION: Completely synthetic amino acid

<400> SEQUENCE: 12

Asp Val Leu Met Thr Gln Ile Pro Leu Ser Leu Pro Val Ser Leu Gly
 1               5                  10                  15

Asp Gln Ala Ser Ile Ser Cys Arg Ser Ser Gln Ser Ile Val His Ser
            20                  25                  30

Asn Gly Asn Thr Tyr Leu Gln Trp Tyr Leu Gln Lys Pro Gly Gln Ser
        35                  40                  45

Pro Lys Leu Leu Ile Tyr Lys Val Ser Asn Arg Leu Tyr Gly Val Pro
    50                  55                  60

Asp Arg Phe Ser Gly Ser Gly Ser Gly Thr Asp Phe Thr Leu Lys Ile
65                  70                  75                  80

Ser Ser Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 13
<211> LENGTH: 117
<212> TYPE: PRT
<213> ORGANISM: Artificial Sequence
<220> FEATURE:
<223> OTHER INFORMATION: Completely synthetic amino acid

<400> SEQUENCE: 13

Asp Val Gln Leu Gln Glu Ser Gly Pro Gly Leu Val Lys Pro Ser Gln
 1               5                  10                  15

Ser Leu Ser Leu Thr Cys Ser Val Thr Gly Tyr Ser Ile Thr Gly Gly
            20                  25                  30

Tyr Leu Trp Asn Trp Ile Arg Gln Phe Pro Gly Asn Lys Leu Glu Trp
        35                  40                  45

Met Gly Tyr Ile Ser Tyr Asp Gly Thr Asn Asn Tyr Lys Pro Ser Leu
    50                  55                  60

Lys Asp Arg Ile Ser Ile Thr Arg Asp Thr Ser Lys Asn Gln Phe Phe
65                  70                  75                  80

Leu Lys Leu Asn Ser Val Thr Asn Glu Asp Thr Ala Thr Tyr Tyr Cys
                85                  90                  95

Ala Arg Tyr Gly Arg Val Phe Phe Asp Tyr Trp Gly Gln Gly Thr Thr
            100                 105                 110

Leu Thr Val Ser Ser
        115
```

Compositions and Methods for Treating Cancer
Sriram Sathyanarayanan et al.
Case No. MRL-ONC-00014-US-PSP

| Gene name | Oligo number | shRNA oligo sequence | % target gene silencing |
|---|---|---|---|
| PIK3CA | OL0003676 | GAAGCAGAAAGGGAAGAAT | 84% |
| PIK3CA | OL0016366 | GCATTGACTAATCAAAGGA | 86% |
| PDPK1 | OL0003618 | GCTGTATTTCGGCCTTAGT | 73% |
| AKT2 | OL0002628 | GATCACTGACTTTGGCCTC | 68% |
| FRAP1/mTOR | OL0002814 | GAGGCATCTCGTTTGTACT | 80% |
| NEK8 | OL0005982 | GCACTGGTGCTGAAGATCA | 70% |
| CCRK | OL0002942 | GGAGATGGAGGACAATCAG | 64% |
| BRAF | OL0022358 | GCACTGATGATGAGAGGTC | 75% |
| MAP2K1 | OL0006008 | GGGAGCTGCAGGTTCTGCA | 86% |
| MAP2K1 | OL0006010 | GGATGACGACTTTGAGAAG | 97% |
| ACK1 | OL0002626 | GAGGCCCACGTCATCCGCT | 79% |
| AURKB | OL0006036 | GGTGATTCACAGAGACATA | 93% |
| BMP2K | OL0023060 | GGATTGTCCAGTCTCCAAC | 96% |
| BUB1 | OL0003702 | GCCCAAGACTGAATTTCAA | 92% |
| BUB1 | OL0023286 | GGGTGTGAAACACATAAGG | 92% |
| CDC2 | OL0008858 | GTCAGTCTTCAGGATGTGC | 85% |
| CIT | OL0024114 | GAAGCTGATGCTAAACTGC | 52% |
| CSK | OL0008340 | GCCTCAGTCATGACGCAAC | 74% |
| CSK | OL0024908 | GCTGGTGGAGCACTACACC | 85% |
| CSNK1A1 | OL0004996 | GCCTCGAAGACCTCTTCAA | 92% |
| CSNK1A1 | OL0004998 | GACTACAATGTACTAGTCA | 89% |
| ERN2 | OL0005850 | GCACTGGTCCACACAGGAG | 66% |
| INSRR | OL0003486 | GCTTCTGTCATGAAAGCCT | 98% |
| MAP2K7 | OL0006020 | GGAAGAGACCAAAGTATAA | 89% |
| MAP3K5 | OL0005876 | GGCATTCATACTGAAATGT | 63% |
| MAP4K5 | OL0002676 | GTTCTGATGGGAGCATGCT | 59% |
| MELK | OL0004990 | GAATGAAGAGTACTTTATG | 88% |
| MYLK2 | OL0005890 | GACTTTGTCTCCAACCTCA | 39% |
| NEK1 | OL0005940 | GCATCCAAATATTGTCCAG | 80% |
| PRKWNK2 | OL0005958 | GAGATGATTGAGTCTGGAT | 80% |
| TGFBR1 | OL0003240 | GACATGATTCAGCCACAGA | 94% |

FIG.10

Compositions and Methods for Treating Cancer
Sriram Sathyanarayanan et al.
Case No. MRL-ONC-00014-US-PSP

| Gene name | Oligo number | ShRNA sequence | Assay |
| --- | --- | --- | --- |
| PIK3CA | OL0016366 | GCATTGACTAATCAAAGGA | Colony outgrowth |
| FRAP1/mTOR | OL0002814 | GAGGCATCTCGTTTGTACT | Colony outgrowth |
| NEK8 | OL0005982 | GCACTGGTGCTGAAGATCA | Colony outgrowth |
| CCRK | OL0002942 | GGAGATGGAGGACAATCAG | 72 h Alamar |
| BRAF | OL0022358 | GCACTGATGATGAGAGGTC | 72 h Alamar |
| MAP2K1 | OL0006010 | GGATGACGACTTTGAGAAG | Colony outgrowth |
| MAP4K5 | OL0002676 | GTTCTGATGGGAGCATGCT | Colony outgrowth |
| MELK | OL0004990 | GAATGAAGAGTACTTTATG | Colony outgrowth |
| MAP2K7 | OL0006020 | GGAAGAGACCAAAGTATAA | Colony outgrowth |
| CIT | OL0024114 | GAAGCTGATGCTAAACTGC | Colony outgrowth |
| MAP3K5 | OL0005876 | GGCATTCATACTGAAATGT | Colony outgrowth |
| PRKWNK2 | OL0005958 | GAGATGATTGAGTCTGGAT | Colony outgrowth |
| MYLK2 | OL0005890 | GACTTTGTCTCCAACCTCA | Colony outgrowth |
| BUB1 | OL0023286 | GGGTGTGAAACACATAAGG | 72 h Alamar |
| CSNK1A1 | OL0004996 | GCCTCGAAGACCTCTTCAA | 72 h Alamar |
| TGFBR1 | OL0003240 | GACATGATTCAGCCACAGA | 72 h Alamar |
| AURKB | OL0006036 | GGTGATTCACAGAGACATA | 72 h Alamar |
| BMP2K | OL0023060 | GGATTGTCCAGTCTCCAAC | 72 h Alamar |
| NTRK3 | OL0004664 | GCATGGAGACCTGAATAAG | 72 h Alamar |

FIG.11

COMPOSITIONS AND METHODS FOR TREATING CANCER

CROSS-REFERENCE TO RELATED APPLICATIONS

The present application is the §371 National Stage application of PCT International Application serial no. PCT/US2010/030074, having an international filing date of Apr. 6, 2010, which claims priority to U.S. Provisional Application Ser. No. 61/169,757, filed Apr. 16, 2009, now expired.

REFERENCE TO SEQUENCE LISTING SUBMITTED ELECTRONICALLY

The sequence listing of the present application is being submitted electronically via EFS-Web as an ASCII formatted sequence listing with a file name "MRLONC00014USPCT-SEQLIST-12OCT2011.txt", creation date of Sep. 12, 2011 and a size of 9,102 bytes. This sequence listing submitted via EFS-Web is part of the specification and is herein incorporated by reference in its entirety.

BACKGROUND OF THE INVENTION

The phosphatidylinositol-3-kinase (PI3K) signaling pathway is important for the growth and survival of cancer cells in many different types of human malignancy. See, Granville C A et al, "Handicapping the Race to Develop Inhibitors of the Phosphoinositide 4-Kinase/Akt/Mammalian Target of Rapamycin Pathway," Clin Cancer Res, 2006; 12(3) 679-89. This pathway receives upstream input from ligand-receptor interactions, such as the epidermal growth factor receptor and insulin-like growth factor receptor, and signals through downstream effectors, such as the mammalian target of rapamycin (mTOR). mTOR is a critical downstream effector molecule that regulates the production of proteins critical for cell cycle progression and many other important cellular growth processes. See, Abraham R T and Gibbons, J J, "The mammalian target of rapamycin signaling pathway: twists and turns in the road to cancer therapy. Clin Cancer Res, 2007; 13(11) 3109-14.

Dysregulation of the PI3 kinase axis is common in human cancer due to overactive growth factor receptor signaling, activating mutations of PI3K, loss of function of the PTEN tumor suppressor, and several other mechanisms that result in activation of mTOR kinase activity. Clinically, successful pharmacological inhibition of the PI3K axis has focused on the upstream growth factor receptors and the downstream effectors of PI3 kinase, such as mTOR. There is now substantial clinical evidence showing that mTOR inhibitors can provide clinical benefit to patients with advanced malignancies.

Insulin-like growth factor receptor 1 (IGF-1R), a tyrosine kinase receptor of the insulin receptor family, is involved in cell proliferation, differentiation, and plays an important role in the transformation and maintenance of malignant cells in many types of cancer. See, Baserga, R, et al., "Mini Review: The IGF-1R receptor in cancer biology," hit. J. Cancer 2003; 107: 873-77. IGR-1R and its ligand IGF-2 are over expressed in many types of advanced cancer, and ligand-stimulated receptor signaling promotes the proliferation of cancer cells in vitro. Significantly, IGF-1R signaling is closely linked to the PI3K axis. IGF-1R inhibition has shown potent anti-cancer effects in preclinical studies, and a number of IGF-1R inhibitors are currently in clinical development.

The combination of mTOR and IGF-1R inhibitors may provide a synergistic effect by inhibiting both upstream and downstream molecular targets in the PI3K axis. The inhibition of mTOR can lead to the activation of a feedback loop that activates the Akt oncogene, which manifests as increased levels of phospho-Akt in tumor cells in vitro and from tumor biopsies taken from patients treated with mTOR inhibitors. See, Sun, S—Y et al., "Priority Report: Activation of Akt and eIF4E survival pathways by rapamycin-mediated mammalian target of rapamycin inhibition," Cancer Res 2005; 65(16): 7052-58, and Gardner, H et al., "Biomarker analysis of a phase II double-blind randomized trial of daily oral RAD001 (everolimus) plus letrozole or placebo plus letrozole as neoadjuvant therapy for patients with estrogen receptor positive breast cancer," San Antonio Breast Cancer Symposium. San Antonio, Tex., Dec. 13-16, 2007. Abstract 2006. This feedback loop can involve signaling through IGF-1R and the insulin receptor substrate, and is inhibited by IGF-1R inhibitors. As a result, preclinical studies have shown that the combination of IGF-1R inhibitors and mTOR inhibitors leads to additive or synergistic anti-tumor activity in vitro. Recently, two groups have independently reported the results of combining rapamycin with anti-IGF-1R antibodies in xenograft models of human sarcomas. See, Kurmasheva R T, et al., Poster: "Combination of CP-751871, a human monoclonal antibody against the IGF-1 receptor with rapamycin results in highly effective therapy for xenografts derived from childhood sarcomas," EORTC 2007, and Darko, I A et al., Abstract: "Evaluation of combined insulin-like growth factor receptor type I (IGF-1R) and mTOR pathway blockade in sarcoma xenograft models. AACR Annual Meeting 2007, 4760. In one of these studies, complete regressions of established Ewing's and osteosarcoma xenografts were observed while in the other potent anti-tumor activity with at least additive benefits from the combination was observed.

SUMMARY OF THE INVENTION

The instant invention provides a method of treating a cancer selected from the group consisting of non-small cell lung cancer, breast cancer, colorectal cancer, soft tissue or bone sarcomas and endometrial cancer with an mTOR inhibitor and an anti-IGF-1R antibody, wherein the mTOR inhibitor is ridaforolimus, everolimus, temsirolimus, a rapamycin-analog or a combination thereof and the anti-IGF-1R antibody is dalotuzumab, figitumumab, cixutumumab, SHC 717454, Roche R1507, EM164 or Amgen AMG479.

BRIEF DESCRIPTION OF THE DRAWINGS

FIG. 10: PI3K and Ras pathway kinases are prominent among the top consensus hits from the MK-0646 enhancer screen. Canonical and putative kinase regulators of the PI3K and Ras pathways are highlighted in red and blue, respectively. Quantitative PCR analysis was performed to assess on target silencing efficiency. The hit validation was performed using colony formation assay or short term growth assays as described in FIGS. 7 and 8.

FIG. 11: Confirmed MK-0646 sensitizing hits. Screening hits that enhanced tumor cell sensitivity to MK-0646 in either a colony outgrowth assay (>2-fold) or in a 72-hr Alamar assay (p<0.05) following exposure to a titration of drug are shown below. Note that certain vectors could not be verified in either assay due to toxicity in the absence of drug. Color coding is as defined in FIG. 10.

DETAILED DESCRIPTION OF THE INVENTION

Figure 1A:
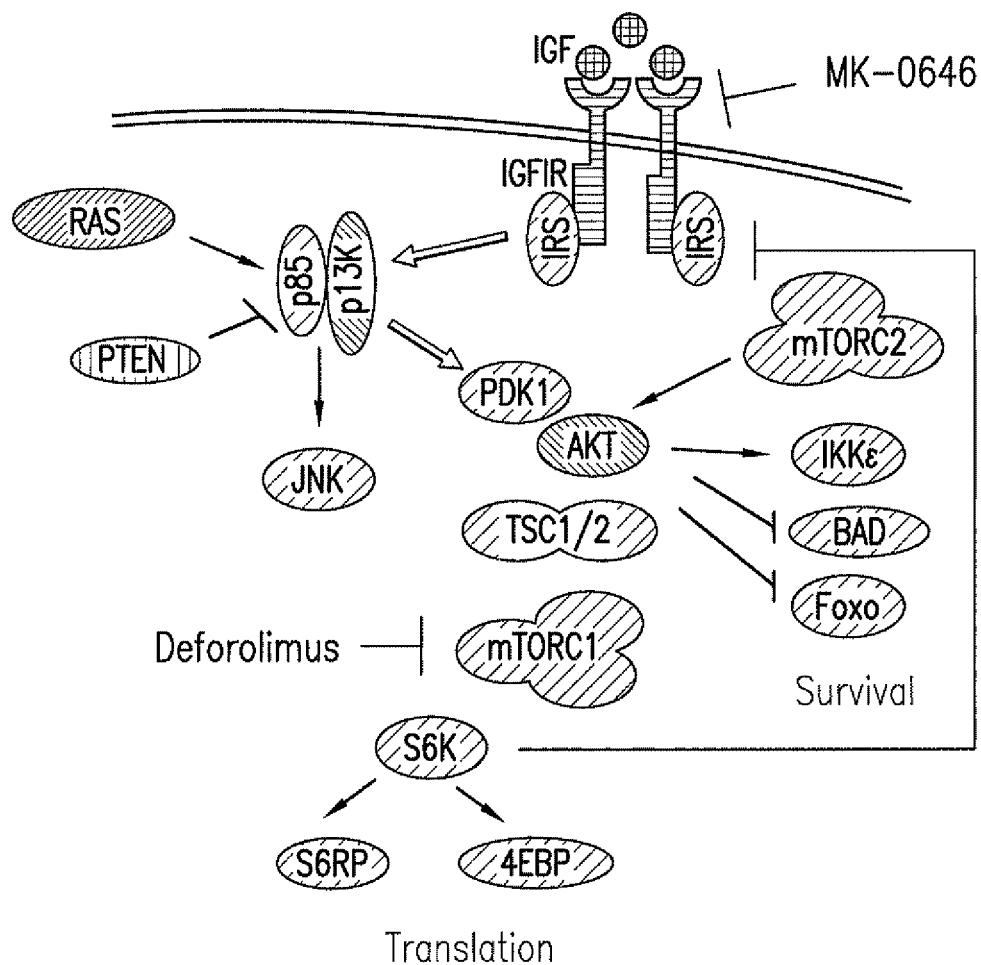
FIG. 1: Improved Targeting of Oncogenic PI3K Signaling with the Ridaforolimus+MK-0646 Combination. Combined treatment with MK-0646 & Ridaforolimus increased PI3K pathway inhibition and blocks cancer cell proliferation. (A) PI3 Kinase signaling pathway illustrating the negative feedback loop; (B) published data demonstrating the mTOR inhibition leads to elevated AKT-P in patient tumors; (C) pathway signaling in response to Ridaforolimus (10 nM), MK-0646 (10 ug/ml) or the combination in H2122 cells in vitro; (D) FACS profile data indicating cell cycle distribution and cell death in cells treated for 24 hours with the treatments indicated at the concentrations used in C.

As a result of assiduous studies, the present inventors have found that a synergistically excellent anticancer activity can be achieved by using an mTOR inhibitor or a pharmaceutically acceptable salt thereof in combination with an anti-IGF-1R antibody, wherein the mTOR inhibitor is ridaforolimus, everolimus, temsirolimus, a rapamycin-analog or a combination thereof, and the anti-IGF-1R antibody is dalotuzumab, figitumumab, cixutumumab, SHC 717454, Roche R1507, EM164 or Amgen AMG479. The invention is especially useful in the treatment of a cancer selected from the group consisting of non-small cell lung cancer, breast cancer, colorectal cancer, soft tissue or bone sarcomas and endometrial cancer. However, the instant invention could prove useful in the treatment of various other cancers, such as brain cancer, cervicocerebral cancer, esophageal cancer, thyroid cancer, small cell lung cancer, lung cancer, stomach cancer, gallbladder/bile duct cancer, liver cancer, pancreatic cancer, ovarian cancer, choriocarcinoma, uterus body cancer, uterocervical cancer, renal pelvis/ureter cancer, bladder cancer, prostate cancer, penis cancer, testicles cancer, fetal cancer, Wilms' cancer, skin cancer, malignant melanoma, neuroblastoma, osteosarcoma, Ewing's tumor, soft part sarcoma, acute leukemia, chronic lymphatic leukemia, chronic myelocytic leukemia and Hodgkin's lymphoma.

Accordingly, the instant invention relates to a method of treating a cancer selected from the group consisting of non-small cell lung cancer, breast cancer, colorectal cancer, soft tissue or bone sarcomas and endometrial cancer with an mTOR inhibitor and an anti-IGF-1R antibody, wherein the mTOR inhibitor is ridaforolimus, everolimus, temsirolimus, a rapamycin-analog or a combination thereof, and the anti-IGF-1R antibody is dalotuzumab, figitumumab, cixutumumab, SHC 717454, Roche R1507, EM164 or Amgen AMG479.

In an embodiment of the invention, the mTOR inhibitor is ridaforolimus.

In another embodiment of the invention, the anti-IGF-1R antibody comprises at least one heavy chain complementary determining region (CDR) of non-human origin and at least one light chain complementary determining region (CDR) derived from a non-human source, wherein said antibody that binds to IGF-IR has at least one of the following properties selected from the group consisting of: a) binding IGF-1R but not IR; (b) binds a hybrid receptor comprising an insulin receptor and insulin growth factor receptor (IR/IGF-1R hybrid-R) but not IR alone; c) inhibiting the binding between a human IGF-1R and IGF-1 and/or IGF-2; (d) binding the hybrid-R and its native ligand, preferably designated herein as IGF1 and/or IGF2 and/or insulin, with an inhibition constant and/or $IC_{50}$ of less than 100 nM; (e) specifically inhibiting the tyrosine kinase activity of said IGF-1R; (f) specifically inhibiting the tyrosine kinase activity of said hybrid-R;

(g) having a binding affinity of 10 nM or less for said hybrid-R; (h) down-regulating IGF-1R expression; (i) down-regulating hybrid-R expression; (j) inhibiting in vivo tumor growth.

In a class of the invention, the heavy chain CDR comprises an amino acid sequence selected from the group consisting of SEQ ID NOs. 4, 5 or 6 and the light chain CDR comprises an amino acid sequence selected from the group consisting of SEQ ID NOs. 1, 2 or 3.

In another class of the invention, the humanized antibody, or one of its functional fragments, comprises a light chain comprising the amino acid sequence selected from the group consisting of SEQ ID No. 7 or 8, or a heavy chain comprising the amino acid sequence selected from the group consisting of SEQ ID NOs.: 9, 10 or 11.

In another class of the invention, the anti-IGF-IR antibody is dalotuzumab.

In another embodiment of the invention, the mTOR inhibitor is ridaforolimus and the anti-IGF-IR antibody is dalotuzumab.

In another embodiment of the invention, the mTOR inhibitor is administered in a dose between 10 mg and 40 mg. In a class of the invention, the ridaforolimus is administered five times a week.

In another embodiment of the invention, the anti-IGF-1R antibody is administered intravenously at a dose of 10 mg/kg. In a class of the invention, the anti-IGF-1R antibody is administered once a week. In another class of the invention, the anti-IGF-1R antibody is administered once every other week.

The mTOR inhibitor and the anti-IGF-1R antibody can be prepared for simultaneous, separate or successive administration.

Reference to the preferred embodiments set forth above is meant to include all combinations of particular and preferred groups unless stated otherwise. The meanings of the terms used in this description are described below, and the invention is described in more detail hereinunder.

The term "simultaneous" as referred to in this description means that the pharmaceutical preparations of the invention are administered simultaneously in time.

The term "separate" as referred to in this description means that the pharmaceutical preparations of the invention are administered at different times during the course of a common treatment schedule.

The term "successive" as referred to in this description means that administration of one pharmaceutical preparation is followed by administration of the other pharmaceutical preparation; after administration of one pharmaceutical preparation, the second pharmaceutical preparation can be administered substantially immediately after the first pharmaceutical preparation, or the second pharmaceutical preparation can be administered after an effective time period after the first pharmaceutical preparation; and the effective time period is the amount of time given for realization of maximum benefit from the administration of the first pharmaceutical preparation.

The term "cancer" as referred to in this description includes various sarcoma and carcinoma and includes solid cancer and hematopoietic cancer. The solid cancer as referred to herein includes, for example, brain cancer, cervicocerebral cancer, esophageal cancer, thyroid cancer, small cell lung cancer, non-small cell lung cancer, breast cancer, endometrial cancer, lung cancer, stomach cancer, gallbladder/bile duct cancer, liver cancer, pancreatic cancer, colon cancer, rectal cancer, ovarian cancer, choriocarcinoma, uterus body cancer, uterocervical cancer, renal pelvis/ureter cancer, bladder cancer, prostate cancer, penis cancer, testicles cancer, fetal cancer, Wilms' tumor, skin cancer, malignant melanoma, neuroblastoma, osteosarcoma, Ewing's tumor, soft part sarcoma. On the other hand, the hematopoietic cancer includes, for example, acute leukemia, chronic lymphatic leukemia, chronic myelocytic leukemia, polycythemia vera, malignant lymphoma, multiple myeloma, Hodgkin's lymphoma, non-Hodgkin's lymphoma.

The term "treatment of cancer" as referred to in this description means that an anticancer agent is administered to a cancer case so as to inhibit the growth of the cancer cells in the case. Preferably, the treatment results in cancer growth regression, or that is, it reduces the size of a detectable cancer. More preferably, the treatment results in complete disappearance of cancer.

mTOR Inhibitors

The mTOR inhibitors in current clinical development are structural analogs of rapamycin. The mTOR inhibitors of the instant invention include ridaforolimus, temsirolimus, everolimus, a rapamycin-analog and combinations thereof.

Ridaforolimus, also known as AP 23573, MK-8669 and deforolimus, is a unique, non-prodrug analog of rapmycin that has antiproliferative activity in a broad range of human tumor cell lines in vitro and in murine tumor xenograft models utilizing human tumor cell lines. Ridaforolimus has been administered to patients with advanced cancer and is currently in clinical development for various advanced malignancies, including studies in patients with advanced soft tissue or bone sarcomas. Thus far, these trials have demonstrated that ridaforolimus is generally well-tolerated with a predictable and manageable adverse even profile, and possess anti-tumor activity in a broad range of cancers. A description and preparation of ridaforolimus is described in U.S. Pat. No. 7,091,213 to Ariad Gene Therapeutics, Inc., which is hereby incorporated by reference in its entirety.

Temsirolimus, also known as Torisel®, is currently marketed for the treatment of renal cell carcinoma. A description and preparation of temsirolimus is described in U.S. Pat. No. 5,362,718 to American Home Products Corporation, which is hereby incorporated by reference in its entirety.

Everolimus, also known as Certican® or RAD001, marketed by Novartis, has greater stability and enhanced solubility in organic solvents, as well as more favorable pharmokinetics with fewer side effects than rapamycin (sirolimus). Everolimus has been used in conjunction with microemulsion cyclosporin (Neoral®, Novartis) to increase the efficacy of the immunosuppressive regime.

The mTOR inhibitors of the instant invention may also exist as various crystals, amorphous substances, pharmaceutically acceptable salts, hydrates and solvates. Further, the mTOR inhibitors of the instant invention may be provided as prodrugs. In general, such prodrugs are functional derivatives of the mTOR inhibitors of the instant invention that can be readily converted into compounds that are needed by living bodies. Accordingly, in the method of treatment of various cancers in the invention, the term "administration" includes not only the administration of a specific compound but also the administration of a compound which, after administered to patients, can be converted into the specific compound in the living bodies. Conventional methods for selection and production of suitable prodrug derivatives are described, for example, in "Design of Prodrugs", ed. H. Bundgaard, Elsevier, 1985, which is referred to herein and is entirely incorporated herein as a part of the present description. Metabolites of the compound may include active compounds that are produced by putting the compound in a biological environment, and are within the scope of the compound in the invention.

Anti-IGF-1R antibodies

The anti-IGF-1R antibodies of the instant invention are isolated antibodies, or functional fragments thereof, wherein said antibody or one of its said fragments being capable of binding specifically to the human insulin-like growth factor I receptor and, if necessary, preferably moreover capable of inhibiting binding of the ligands IGF I and/or IGF2 to IGF-IR and/or capable of specifically inhibiting the signaling cascade attendant to the binding of at least one ligand to said IGF-IR receptor. The IGF-1R antibodies of the instant invention include monoclonal and/or polyclonal antibodies, specifically capable of binding IGF-1R. The anti-IGF-IR antibodies of the instant invention include dalotuzumab, figitumumab, cixutumumab, SHC 717454, Roche R1507, EM164 and Amgen AMG479.

Dalotuzumab is characterized in that it comprises a light chain comprising at least one complementarity determining region CDR chosen from the CDRs of amino acid sequence SEQ ID Nos. 1, 2 or 3, or at least one CDR whose sequence has at least 80%, preferably 85%, 90%, 95% and 98% identity, after optimum alignment, with the sequence SEQ ID Nos. 1, 2 or 3, or in that it comprises a heavy chain comprising at least one CDR chosen from the CDRs of amino acid sequence SEQ ID Nos. 4, 5 and 6, or at least one CDR whose sequence has at least 80%, preferably 85%, 90%, 95% and 98% identity, after optimum alignment, with the sequence SEQ ID No. 4, 5 and 6. Methods for making and using said anti-IGF-1R antibody are described in U.S. Pat. No. 7,214,444, which is hereby incorporated by reference in its entirety.

In the present description, the terms "to bind" and "to attach" have the same meaning and are inter-changeable.

In the present description, the terms polypeptides, polypeptide sequences, peptides and proteins attached to antibody compounds or to their sequence are interchangeable.

It must be understood here that the invention does not relate to the antibodies in natural form, that is to say they are not in their natural environment but that they have been able to be isolated or obtained by purification from natural sources, or else obtained by genetic recombination, or by chemical synthesis, and that they can then contain unnatural amino acids as will be described further on.

By CDR region or CDR, it is intended to indicate the hypervariable regions of the heavy and light chains of the immunoglobulins as defined by Kabat et al. (Kabat et al., Sequences of proteins of immunological interest, 5th Ed., U.S. Department of Health and Human Services, NIH, 1991, and later editions). 3 heavy chain CDRs and 3 light chain CDRs exist. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

By "percentage of identity" between two nucleic acid or amino acid sequences in the sense of the present invention, it is intended to indicate a percentage of nucleotides or of identical amino acid residues between the two sequences to be compared, obtained after the best alignment (optimum alignment), this percentage being purely statistical and the differences between the two sequences being distributed randomly and over their entire length. The comparisons of sequences between two nucleic acid or amino acid sequences are traditionally carried out by comparing these sequences after having aligned them in an optimum manner, said comparison being able to be carried out by segment or by "comparison window". The optimum alignment of the sequences for the comparison can be carried out, in addition to manually, by means of the local homology algorithm of Smith and Waterman (1981) [Ad. App. Math. 2:482], by means of the local homology algorithm of Neddleman and Wunsch (1970) [J. Mol. Biol. 48: 443], by means of the similarity search method of Pearson and Lipman (1988) [Proc. Natl. Acad. Sci. USA 85:2444), by means of computer software using these algorithms (GAP, BESTFIT, FASTA and TFASTA in the Wisconsin Genetics Software Package, Genetics Computer Group, 575 Science Dr., Madison, Wis., or else by BLAST N or BLAST P comparison software).

The percentage of identity between two nucleic acid or amino acid sequences is determined by comparing these two sequences aligned in an optimum manner and in which the nucleic acid or amino acid sequence to be compared can comprise additions or deletions with respect to the reference sequence for an optimum alignment between these two sequences. The percentage of identity is calculated by determining the number of identical positions for which the nucleotide or the amino acid residue is identical between the two sequences, by dividing this number of identical positions by the total number of positions in the comparison window and by multiplying the result obtained by 100 in order to obtain the percentage of identity between these two sequences.

For example, it is possible to use the BLAST program, "BLAST 2 sequences" (Tatusova et al., "Blast 2 sequences—a new tool for comparing protein and nucleotide sequences", FEMS Microbiol Lett. 174:247-250) available on the site http://www.ncbi.nlm.nih.gov/gorf/b12.html, the parameters used being those given by default (in particular for the parameters "open gap penalty": 5, and "extension gap penalty: 2; the matrix chosen being, for example, the matrix "BLOSUM 62" proposed by the program), the percentage of identity between the two sequences to be compared being calculated directly by the program.

By amino acid sequence having at least 80%, preferably 85%, 90%, 95% and 98% identity with a reference amino acid sequence, those having, with respect to the reference sequence, certain modifications, in particular a deletion, addition or substitution of at least one amino acid, a truncation or an elongation are preferred. In the case of a substitution of one or more consecutive or nonconsecutive amino acid(s), the substitutions are preferred in which the substituted amino acids are replaced by "equivalent" amino acids. The expression "equivalent amino acids" is aimed here at indicating any amino acid capable of being substituted with one of the amino acids of the base structure without, however, essentially modifying the biological activities of the corresponding antibodies and such as will be defined later, especially in the examples.

These equivalent amino acids can be determined either by relying on their structural homology with the amino acids which they replace, or on results of comparative trials of biological activity between the different antibodies capable of being carried out.

By way of example, mention is made of the possibilities of substitution capable of being carried out without resulting in a profound modification of the biological activity of the corresponding modified antibody. It is thus possible to replace leucine by valine or isoleucine, aspartic acid by glutamic acid, glutamine by asparagine, arginine by lysine, etc., the reverse substitutions being naturally envisageable under the same conditions.

The antibodies according to the present invention are preferably specific monoclonal antibodies, especially of murine, chimeric or humanized origin, which can be obtained according to the standard methods well known to the person skilled in the art.

In general, for the preparation of monoclonal antibodies or their functional fragments, especially of murine origin, it is possible to refer to techniques which are described in particular in the manual "Antibodies" (Harlow and Lane, Antibodies: A Laboratory Manual, Cold Spring Harbor Laboratory, Cold Spring Harbor N.Y., pp. 726, 1988) or to the technique of preparation from hybridomas described by Kohler and Milstein (Nature, 256:495-497, 1975).

The monoclonal antibodies according to the invention can be obtained, for example, from an animal cell immunized against the IGF-IR receptor, or one of its fragments containing the epitope specifically recognized by said monoclonal antibodies according to the invention. Said IGF-IR receptor, or one of its said fragments, can especially be produced according to the usual working methods, by genetic recombination starting with a nucleic acid sequence contained in the cDNA sequence coding for the IGF-IR receptor or by peptide synthesis starting from a sequence of amino acids comprised in the peptide sequence of the IGF-IR receptor.

The monoclonal antibodies according to the invention can, for example, be purified on an affinity column on which the IGF-IR receptor or one of its fragments containing the epitope specifically recognized by said monoclonal antibodies according to the invention has previously been immobilized. More particularly, said monoclonal antibodies can be purified by chromatography on protein A and/or G, followed or not followed by ion-exchange chromatography aimed at eliminating the residual protein contaminants as well as the DNA and the LPS, in itself followed or not followed by exclusion chromatography on Sepharose gel in order to eliminate the potential aggregates due to the presence of dimers or of other multimers. In an even more preferred manner, the whole of these techniques can be used simultaneously or successively.

Chimeric or humanized antibodies are likewise included in antibodies according to the present invention.

By chimeric antibody, it is intended to indicate an antibody which contains a natural variable (light chain and heavy chain) region derived from an antibody of a given species in combination with the light chain and heavy chain constant regions of an antibody of a species heterologous to said given species.

The antibodies or their fragments of chimeric type according to the invention can be prepared by using the techniques of genetic recombination. For example, the chimeric antibody can be produced by cloning a recombinant DNA containing a promoter and a sequence coding for the variable region of a nonhuman, especially murine, monoclonal antibody according to the invention and a sequence coding for the constant region of human antibody. A chimeric antibody of the invention encoded by such a recombinant gene will be, for example, a mouse-man chimera, the specificity of this antibody being determined by the variable region derived from the murine DNA and its isotype determined by the constant region derived from the human DNA. For the methods of preparation of chimeric antibodies, it is possible, for example, to refer to the document Verhoeyn et al. (BioEssays, 8:74, 1988).

By humanized antibody, it is intended to indicate an antibody which contains CDR regions derived from an antibody of nonhuman origin, the other parts of the antibody molecule being derived from one (or from several) human antibodies. Moreover, some of the residues of the segments of the skeleton (called FR) can be modified in order to conserve the affinity of the binding (Jones et al., Nature, 321:522-525, 1986; Verhoeyen et al., Science, 239:1534-1536, 1988; Riechmann et al., Nature, 332:323-327, 1988).

The humanized antibodies according to the invention or their fragments can be prepared by techniques known to the person skilled in the art (such as, for example, those described in the documents Singer et al., J. Immure. 150:2844-2857, 1992; Mountain et al., Biotechnol. Genet. Eng. Rev., 10:1-142, 1992; or Bebbington et al., Bio/Technology, 10:169-175, 1992). Such humanized antibodies according to the invention are preferred for their use in in vitro diagnostic methods, or in vivo prophylactic and/or therapeutic treatment.

By functional fragment of an antibody according to the invention, it is intended to indicate in particular an antibody fragment, such as Fv, scFv (sc for single chain), Fab, F(ab')$_2$, Fab', scFv-Fc fragments or diabodies, or any fragment of which the half-life time would have been increased by chemical modification, such as the addition of poly(alkylene) glycol such as poly(ethylene) glycol ("PEGylation") (pegylated fragments called Fv-PEG, scFv-PEG, Fab-PEG, F(ab')$_2$—PEG or Fab'-PEG) ("PEG" for Poly(Ethylene) Glycol), or by incorporation in a liposome, said fragments having at least one of the characteristic CDRs of sequence SEQ ID No. 1, 2, 3, 4, 5 or 6 according to the invention, and, especially, in that it is capable of exerting in a general manner an even partial activity of the antibody from which it is descended, such as in particular the capacity to recognize and to bind to the IGF-IR receptor, and, if necessary, to inhibit the activity of the IGF-IR receptor.

Preferably, said functional fragments will be constituted or will comprise a partial sequence of the heavy or light variable chain of the antibody from which they are derived, said partial sequence being sufficient to retain the same specificity of binding as the antibody from which it is descended and a sufficient affinity, preferably at least equal to 1/100, in a more preferred manner to at least 1/10, of that of the antibody from which it is descended, with respect to the IGF-IR receptor.

Such a functional fragment will contain at the minimum 5 amino acids, preferably 10, 15, 25, 50 and 100 consecutive amino acids of the sequence of the antibody from which it is descended.

Preferably, these functional fragments will be fragments of Fv, scFv, Fab, F(ab')$_2$, F(ab'), scFv-Fc type or diabodies, which generally have the same specificity of binding as the antibody from which they are descended. According to the present invention, antibody fragments of the invention can be obtained starting from antibodies such as described above by methods such as digestion by enzymes, such as pepsin or papain and/or by cleavage of the disulfide bridges by chemical reduction. In another manner, the antibody fragments comprised in the present invention can be obtained by techniques of genetic recombination likewise well known to the person skilled in the art or else by peptide synthesis by means of, for example, automatic peptide synthesizers such as those supplied by the company Applied Biosystems, etc.

In a more preferred manner, the invention comprises the antibodies, or their functional fragments, according to the present invention, especially chimeric or humanized antibodies, obtained by genetic recombination or by chemical synthesis.

In a preferred embodiment, a subject of the invention is an antibody, or one of its functional fragments, according to the invention, characterized in that it comprises a heavy chain comprising at least one CDR of sequence SEQ ID No. 6 or a sequence having at least 80% identity after optimum alignment with the sequence SEQ ID No. 6.

Among the six short CDR sequences, the third CDR of the heavy chain (CDRH3) has a greater size variability (greater diversity essentially due to the mechanisms of arrangement of the genes which give rise to it). It can be as short as 2 amino acids although the longest size known is 26. Functionally, CDRH3 plays a role in part in the determination of the specificity of the antibody (Segal et al., PNAS, 71:4298-4302, 1974; Amit et al., Science, 233:747-753, 1986; Chothia et al., J. Mol. Biol., 196:901-917, 1987; Chothia et al., Nature, 342:877-883, 1989; Caton et al., J. Immuno, 144:1965-1968, 1990; Sharon et al., PNAS, 87:4814-4817, 1990; Sharon et al., J. Immunol., 144:4863-4869, 1990; Kabat et al., J. Immunol., 147:1709-1719, 1991).

It is known that only a low percentage of the amino acids of the CDRs contribute to the construction of an antibody binding site, but these residues must be maintained in a very specific tridimensional conformation.

In a more preferred manner, the present invention relates to an antibody or one of its functional fragments, according to the invention, characterized in that it comprises a heavy chain comprising at least two of the three CDRs or the three CDRs of sequence SEQ ID Nos. 4, 5 and 6, or at least two of three CDRs or three CDRs of sequence respectively having at least 80% identity after optimum alignment with the sequence SEQ ID No. 4, 5 and 6.

In a likewise preferred embodiment, a subject of the invention is an antibody or one of its functional fragments, according to the invention, characterized in that it comprises a light chain comprising at least one CDR chosen from the CDRs of sequence SEQ ID No. 1, 2 or 3, or a CDR whose sequence has at least 80% identity after optimum alignment with the sequence SEQ ID No. 1, 2 or 3.

In a more preferred embodiment, a subject of the invention is an antibody or one of its functional fragments according to the invention, characterized in that it comprises a light chain comprising at least two of the three CDRs or the three CDRs of sequence SEQ ID Nos. 1, 2 and 3, or at least two of three CDRs or three CDRs of sequence respectively having at least 80% identity after optimum alignment with the sequence SEQ ID No. 1, 2 and 3.

In a more preferred manner, the antibody or one of its functional fragments according to the invention is characterized in that it comprises a heavy chain comprising the three CDRs of sequence SEQ ID Nos. 4, 5 and 6, or three CDRs of sequence respectively having at least 80% of identity after optimum alignment with the sequence SEQ ID No. 4, 5 and 6 and in that it moreover comprises a light chain comprising the three CDRs of sequence SEQ ID Nos. 1, 2 and 3, or three CDRs of sequence respectively having at least 80% of identity after optimum alignment with the sequence SEQ ID No. 1, 2 and 3.

According to another aspect, a subject of the present invention is an antibody or one of its functional fragments, according to the invention, characterized in that it does not attach or it does not attach in a significant manner to the human insulin receptor IR.

In a preferred manner, said functional fragments according to the present invention will be chosen from the fragments Fv, scFv, Fab, (Fab')$_2$, Fab', scFv-Fc or diabodies, or any functional fragment whose half-life would have been increased by a chemical modification, especially by PEGylation, or by incorporation in a liposome.

According to another aspect, the invention relates to a murine hybridoma capable of secreting a monoclonal antibody according to the present invention, especially the hybridoma of murine origin such as deposited at the Centre National de Culture De Microorganisme (CNCM, National Center of Microorganism Culture) (Institut Pasteur, Paris, France) on Sep. 19, 2001 under the number 1-2717.

The monoclonal antibody here called 7C10, or one of its functional fragments, characterized in that said antibody is secreted by the hybridoma deposited at the CNCM on Sep. 19, 2001 under the number 1-2717 is, of course, part of the present invention.

"Dalotuzumab," "h7C10," "MK-0646," or "F50035" are used interchangeably to describe a humanized antibody that is characterized as binding IGF-1R as well as binding the IR/IGF-1 hybrid receptor. Such an antibody may include the antibody described, for example, in U.S. Ser. No. 10/735,916 (US20050084906), which is CIP of PCT/FR03/00178 and/or US20050249730, wherein said is a humanized antibody or a fragment thereof and comprises a light chain and/or a heavy chain in which the skeleton segments FR1 to FR4 of said light chain and/or heavy chain are respectively derived from skeleton segments FR1 to FR4 of human antibody light chain and/or heavy chain. The humanized antibody may comprise at least one light chain that comprises at least one or more complementary determining regions derived from a non-human source and having the amino acid sequence selected from the group consisting of SEQ ID NOs: 1, 2 or 3 and at least one heavy chain comprising at least one or more complementary determining regions having an amino acid sequence selected from the group consisting of SEQ ID NOs 4, 5, or 6. The light chain may comprise one or more of the amino acid sequences as set forth in one of SEQ ID No. 7 or 8, or a sequence having at least 80% identity after optimum alignment with the sequence SEQ ID No. 7 or 8. Likewise, the heavy chain comprises one or more amino acid sequences as set forth in one of SEQ ID No. 9, 10 or 11, or a sequence having at least 80% identity after optimum alignment with the sequence SEQ ID No. 9, 10 or 11.

In a particular embodiment, the present invention relates to a murine antibody, or one of its functional fragments, according to the invention, characterized in that said antibody comprises a light chain of sequence comprising the amino acid sequence SEQ ID No. 12, or a sequence having at least 80% identity after optimum alignment with the sequence SEQ ID No. 12, or/and in that it comprises a heavy chain of sequence comprising the amino acid sequence SEQ ID No. 13, or a sequence having at least 80% identity after optimum alignment with the sequence SEQ ID No. 13.

Figitumumab, also known as CP 751,871, is a fully human antibody under investigation by Pfizer. A description and preparation of figitumumab is described in U.S. Pat. No. 7,037,498 to Abgenix, Inc and Pfizer, Inc., which is hereby incorporated by reference in its entirety.

Cixutumumab, also known as IMC A-12, is a fully human antibody under investigation by ImClone. A description and preparation of cixutumumab is described in U.S. Patent Publication No. US2008/0025990, which is hereby incorporated by reference in its entirety.

SHC717454, also known as CP 751,871, is a fully human antibody under investigation by Schering Plough (now Merck & Co., Inc.). A description and preparation of SHC717454 is described in U.S. Pat. No. 7,217,796 to Schering Corporation, which is hereby incorporated by reference in its entirety.

Roche R1507, is under investigation by Hoffmann-LaRoche. A description and preparation of Roche R1507 is described in U.S. Pat. No. 7,378,503 to Hoffmann-Laroche, Inc., which is hereby incorporated by reference in its entirety.

EM164, is under investigation by Immuogen. A description and preparation of EM164 is described in International Patent Publication WO03/106621 to Immunogen, Inc., which is hereby incorporated by reference in its entirety Amgen AMG479, is under investigation by Amgen, Inc. A description and preparation of Amgen AMG479 is described in International Patent Publication WO06/069202 to Amgen, Inc., which is hereby incorporated by reference in its entirety.

According to a likewise particular aspect, the present invention relates to a chimeric antibody, or one of its functional fragments, according to the invention, characterized in that said antibody moreover comprises the light chain and heavy chain constant regions derived from an antibody of a species heterologous to the mouse, especially man, and in a preferred manner in that the light chain and heavy chain constant regions derived from a human antibody are respectively the kappa and gamma-1, gamma-2 or gamma-4 region.

According to a likewise particular aspect, the present invention relates to a humanized antibody or one of its functional fragments, according to the invention, characterized in that said antibody comprises a light chain and/or a heavy chain in which the skeleton segments FR1 to FR4 (such as defined below in examples 12 and 13, in tables 5 and 6) of said light chain and/or heavy chain are respectively derived from skeleton segments FR1 to FR4 of human antibody light chain and/or heavy chain.

Preferably, the humanized antibody, or one of its functional fragments, according to the invention is characterized in that said humanized antibody comprises a light chain comprising the amino acid sequence SEQ ID No. 8, and in that it comprises a heavy chain of sequence comprising the amino acid sequence SEQ ID No. 10 or 11, preferably SEQ ID No. 11.

By nucleic acid, nucleic or nucleic acid sequence, polynucleotide, oligonucleotide, polynucleotide sequence, nucleotide sequence, terms which will be employed indifferently in the present invention, it is intended to indicate a precise linkage of nucleotides, which are modified or unmodified, allowing a fragment or a region of a nucleic acid to be defined, containing or not containing unnatural nucleotides, and being able to correspond just as well to a double-stranded DNA, a single-stranded DNA as to the transcription products of said DNAs.

It must also be understood here that the present invention does not concern the nucleotide sequences in their natural chromosomal environment, that is to say, in the natural state. It concerns sequences which have been isolated and/or purified, that is to say that they have been selected directly or indirectly, for example by copy, their environment having been at least partially modified. It is thus likewise intended to indicate here the isolated nucleic acids obtained by genetic recombination by means, for example, of host cells or obtained by chemical synthesis.

By nucleic sequences having a percentage of identity of at least 80%, preferably 85%, 90%, 95% and 98%, after optimum alignment with a preferred sequence, it is intended to indicate the nucleic sequences having, with respect to the reference nucleic sequence, certain modifications such as, in particular, a deletion, a truncation, an elongation, a chimeric fusion and/or a substitution, especially point substitution. It preferably concerns sequences in which the sequences code for the same amino acid sequences as the reference sequence, this being connected to the degeneracy of the genetic code, or complementary sequences which are capable of hybridizing specifically with the reference sequences, preferably under conditions of high stringency, especially such as defined below.

A hybridization under conditions of high stringency signifies that the temperature conditions and ionic strength conditions are chosen in such a way that they allow the maintenance of the hybridization between two fragments of complementary DNA. By way of illustration, conditions of high stringency of the hybridization step for the purposes of defining the polynucleotide fragments described above are advantageously the following.

The DNA-DNA or DNA-RNA hybridization is carried out in two steps: (1) prehybridization at 42° C. for 3 hours in phosphate buffer (20 mM, pH 7.5) containing 5×SSC (1×SSC corresponds to a 0.15 M NaCl+0.015 M sodium citrate solution), 50% of formamide, 7% of sodium dodecyl sulfate (SDS), 10×Denhardt's, 5% of dextran sulfate and 1% of salmon sperm DNA; (2) actual hybridization for 20 hours at a temperature dependent on the size of the probe (i.e.: 42° C., for a probe size >100 nucleotides) followed by 2 washes of 20 minutes at 20° C. in 2×SSC+2% of SDS, I wash of 20 minutes at 20° C. in 0.1×SSC+0.1% of SDS. The last wash is carried out in 0.1×SSC+0.1% of SDS for 30 minutes at 60° C. for a probe size >100 nucleotides. The hybridization conditions of high stringency described above for a polynucleotide of defined size can be adapted by the person skilled in the art for oligonucleotides of greater or smaller size, according to the teaching of Sambrook et al., (1989, Molecular cloning: a laboratory manual. 2nd Ed. Cold Spring Harbor).

Dosing and Routes of Administration

With regard to the mTOR inhibitors and anti-IGF-1R antibodies of the invention, various preparation forms can be selected, and examples thereof include oral preparations such as tablets, capsules, powders, granules or liquids, or sterilized liquid parenteral preparations such as solutions or suspensions, suppositories, ointments and the like. The mTOR inhibitors are available as pharmaceutically acceptable salts. The mTOR inhibitors and anti-IGF-1R antibodies of the invention are prepared with pharmaceutically acceptable carriers or diluents.

The term "pharmaceutically acceptable salt" as referred to in this description means ordinary, pharmaceutically acceptable salt. For example, when the compound has a hydroxyl group, or an acidic group such as a carboxyl group and a tetrazolyl group, then it may form a base-addition salt at the hydroxyl group or the acidic group; or when the compound has an amino group or a basic heterocyclic group, then it may form an acid-addition salt at the amino group or the basic heterocyclic group.

The base-addition salts include, for example, alkali metal salts such as sodium salts, potassium salts; alkaline earth metal salts such as calcium salts, magnesium salts; ammonium salts; and organic amine salts such as trimethylamine salts, triethylamine salts, dicyclohexylamine salts, ethanolamine salts, diethanolamine salts, triethanolamine salts, procaine salts, N,N'-dibenzylethylenediamine salts.

The acid-addition salts include, for example, inorganic acid salts such as hydrochlorides, sulfates, nitrates, phosphates, perchlorates; organic acid salts such as maleates, fumarates, tartrates, citrates, ascorbates, trifluoroacetates; and sultanates such as methanesulfonates, isethionates, benzenesulfonates, p-toluenesulfonates.

The term "pharmaceutically acceptable carrier or diluent" refers to excipients [e.g., fats, beeswax, semi-solid and liquid polyols, natural or hydrogenated oils, etc.]; water (e.g., distilled water, particularly distilled water for injection, etc.), physiological saline, alcohol (e.g., ethanol), glycerol, polyols, aqueous glucose solution, mannitol, plant oils, etc.); additives [e.g., extending agent, disintegrating agent, binder, lubricant, wetting agent, stabilizer, emulsifier, dispersant, preservative, sweetener, colorant, seasoning agent or aromatizer, concentrating agent, diluent, buffer substance, solvent or solubilizing agent, chemical for achieving storage effect, salt for modifying osmotic pressure, coating agent or antioxidant], and the like.

Solid preparations can be prepared in the forms of tablet, capsule, granule and powder without any additives, or prepared using appropriate carriers (additives). Examples of such carriers (additives) may include saccharides such as lactose or glucose; starch of corn, wheat or rice; fatty acids such as stearic acid; inorganic salts such as magnesium meta silicate aluminate or anhydrous calcium phosphate; synthetic polymers such as polyvinylpyrrolidone or polyalkylene glycol; alcohols such as stearyl alcohol or benzyl alcohol; synthetic cellulose derivatives such as methylcellulose, carboxymethylcellulose, ethylcellulose or hydroxypropylmethylcellulose; and other conventionally used additives such as gelatin, talc, plant oil and gum arabic.

These solid preparations such as tablets, capsules, granules and powders may generally contain, for example, 0.1 to 100% by weight, and preferably 5 to 98% by weight, of the mTOR inhibitor, based on the total weight of each preparation.

Liquid preparations are produced in the forms of suspension, syrup, injection and drip infusion (intravenous fluid) using appropriate additives that are conventionally used in liquid preparations, such as water, alcohol or a plant-derived oil such as soybean oil, peanut oil and sesame oil.

In particular, when the preparation is administered parenterally in a form of intramuscular injection, intravenous injection or subcutaneous injection, appropriate solvent or diluent may be exemplified by distilled water for injection, an aqueous solution of lidocaine hydrochloride (for intramuscular injection), physiological saline, aqueous glucose solution, ethanol, polyethylene glycol, propylene glycol, liquid for intravenous injection (e.g., an aqueous solution of citric acid, sodium citrate and the like) or an electrolytic solution (for intravenous drip infusion and intravenous injection), or a mixed solution thereof.

Such injection may be in a form of a preliminarily dissolved solution, or in a form of powder per se or powder associated with a suitable carrier (additive) which is dissolved at the time of use. The injection liquid may contain, for example, 0.1 to 10% by weight of an active ingredient based on the total weight of each preparation.

Liquid preparations such as suspension or syrup for oral administration may contain, for example, 0.1 to 10% by weight of an active ingredient based on the total weight of each preparation.

Each preparation in the invention can be prepared by a person having ordinary skill in the art according to conventional methods or common techniques. For example, a preparation can be carried out, if the preparation is an oral preparation, for example, by mixing an appropriate amount of the compound of the invention with an appropriate amount of lactose and filling this mixture into hard gelatin capsules which are suitable for oral administration. On the other hand, preparation can be carried out, if the preparation containing the compound of the invention is an injection, for example, by mixing an appropriate amount of the compound of the invention with an appropriate amount of 0.9% physiological saline and filling this mixture in vials for injection.

The components of this invention may be administered to mammals, including humans, either alone or, in combination with pharmaceutically acceptable carriers, excipients or diluents, in a pharmaceutical composition, according to standard pharmaceutical practice. The components can be administered orally or parenterally, including the intravenous, intramuscular, intraperitoneal, subcutaneous, rectal and topical routes of administration.

Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved. Further information about suitable dosages is provided below.

The term "administration" and variants thereof (e.g., "administering" a compound) in reference to a component of the invention means introducing the component or a prodrug of the component into the system of the animal in need of treatment. When a component of the invention or prodrug thereof is provided in combination with one or more other active agents (e.g., the mTOR inhibitor), "administration" and its variants are each understood to include concurrent and sequential introduction of the component or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

A suitable amount of an mTOR inhibitor is administered to a patient undergoing treatment for cancer. In an embodiment, the mTOR inhibitor is administered in doses from about 10 mg-40 mg per day. In an embodiment of the invention, the mTOR inhibitor is administered in a dose of 10 mg per day. In another embodiment of the invention, the mTOR inhibitor is administered in a dose of 20 mg per day. In another embodiment of the invention, the mTOR inhibitor is administered in a dose of 30 mg per day. In another embodiment of the invention, the mTOR inhibitor is administered in a dose of 40 mg per day.

In an embodiment of the invention, the mTOR inhibitor can be administered 5 times per week. For example, ridaforolimus is started on Day 1, and continued at the specified dosing level for five consecutive days, followed by two days of no ridaforolimus treatment. Ridaforolimus is then continued on this daily X 5 schedule each week.

The combination therapeutic comprising the anti-IGF-1R antibodies and mTOR inhibitors of the invention are administered to a human patient, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody is preferred. Three distinct delivery approaches are expected to be useful for delivery of the antibodies in accordance with the invention. Conventional intravenous delivery will presumably be the standard delivery technique for the majority of tumours. However, in connection with some tumours, such as those in the peritoneal cavity exemplified by tumours of the ovaries, biliary duct, other ducts, and the like, intraperitoneal administration may prove favorable for obtaining high dose of antibody at the tumour and to minimize antibody clearance. In a similar manner certain solid tumours possess vasculature that is appropriate for regional perfusion. Regional perfusion will allow the obtention of a high dose of the antibody at the site of a tumour and will minimize short term clearance of the antibody.

As with any protein or antibody infusion based therapeutic, safety concerns are related primarily to (i) cytokine release syndrome, i.e., hypotension, fever, shaking, chills, (ii) the development of an immunogenic response to the material (i.e., development of human antibodies by the patient to the antibody therapeutic, or HAHA or HACA response), and (iii) toxicity to normal cells that express the EGF receptor, e.g., hepatocytes which express EGFR and/or IGF-1R. Standard tests and follow up will be utilized to monitor each of these safety concerns. In particular, liver function will be monitored frequently during clinical trails in order to assess damage to the liver, if any.

For the prevention or treatment of disease, the appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. In a combination therapy regimen, the compositions of the present invention are administered in a therapeutically effective or synergistic amount. As used herein, a therapeutically effective amount is such that co-administration of anti-IGF-1R antibody and the mTOR inhibitor, or administration of a composition of the present invention, results in reduction or inhibition of the targeting disease or condition. A therapeutically synergistic amount is that amount of anti-IGF-1R antibody and mTOR inhibitor necessary to synergistically or significantly reduce or eliminate conditions or symptoms associated with a particular disease.

In a broad embodiment, the treatment of the present invention involves the combined administration of an anti-IGF-1R antibody and an mTOR inhibitor. The combined administration includes co administration, using separate formulations or a single pharmaceutical formulation, and consecutive administration in either order, wherein preferably there is a time period while both (or all) active agents simultaneously exert their biological activities. Preparation and dosing schedules for such chemotherapeutic agents may be used according to manufacturers' instructions or as determined empirically by the skilled practitioner. Preparation and dosing schedules for chemotherapy are also described in Chemotherapy Service Ed., M. C. Perry, Williams & Wilkins, Baltimore, Md. (1992). The mTOR inhibitor may precede, or follow administration of the antibody or may be given simultaneously therewith. The clinical dosing of therapeutic combination of the present invention are likely to be limited by the extent of adverse reactions.

Depending on the type and severity of the disease, about 1 µg/kg to 50 mg/kg (e.g. 0.1-20 mg/kg) of antibody is an initial candidate dosage for administration to the patient, whether, for example, by one or more separate administrations, or by continuous infusion. A typical daily dosage might range from about 1 µg/kg to about 100 mg/kg or more, depending on the factors mentioned above. For repeated administrations over several days or longer, depending on the condition, the treatment is sustained until a desired suppression of disease symptoms occurs. However, other dosage regimens may be useful.

In one aspect, the antibody of the invention is administered weekly or may be administered every two to three weeks, at a dose ranged from about 5 mg/kg to about 15 mg/kg. In some aspects, the chemotherapy regimen involves the traditional high-dose intermittent administration. In some other aspects, the chemotherapeutic agents are administered using smaller and more frequent doses without scheduled breaks ("metronomic chemotherapy"). The progress of the therapy of the invention is easily monitored by conventional techniques and assays.

In one embodiment, the dosing sequence comprises administering the mTOR inhibitor concurrently with the IGF-1R antibody—for example, ridaforolimus is administered everyday while the IGF-1R antibody (dalotuzumab) is administered weekly. In particular, dalotuzumab is administered at a dose of 10 mg/kg i.v weekly while ridaforolimus is administered at 10 mg on a daily schedule.

In another embodiment, the dosing sequence comprises administering the mTOR inhibitor concurrently with the IGF-1R antibody—for example, ridaforolimus is administered everyday while the IGF-1R antibody (dalotuzumab) is administered weekly. In particular, dalotuzumab is administered at a dose of 10 mg/kg i.v weekly while ridaforolimus is administered at 20 mg on a daily schedule.

In one embodiment, the dosing sequence comprises administering the mTOR inhibitor concurrently with the IGF-1R antibody—for example, ridaforolimus is administered everyday while the IGF-1R antibody (dalotuzumab) is administered weekly. In particular, dalotuzumab is administered at a dose of 10 mg/kg i.v weekly while ridaforolimus is administered at 30 mg on a daily schedule.

In one embodiment, the dosing sequence comprises administering the mTOR inhibitor concurrently with the IGF-1R antibody—for example, ridaforolimus is administered everyday while the IGF-1R antibody (dalotuzumab) is administered weekly. In particular, dalotuzumab is administered at a dose of 10 mg/kg i.v weekly while ridaforolimus is administered at 40 mg on a daily schedule.

Alternative dosing regimens for the IGF-1R antibody are as follows: (a) 15 mg/kg loading, followed by 7.5 mg/kg every week; (b) 7.5 mg/kg per week; (c) 10.0 mg/kg per week; (d) 7.5 mg/kg every other week; (e) 10.0 mg/kg every other week; (f) 20 mg/kg every other week; (g) 30 mg/kg every three weeks.

Sample dosing regimens for the combination are as follows:

| Sample regimen | mTOR inhibitor (mg/day QDX5) | Anti-IGF-1R antibody |
|---|---|---|
| 1 | 10 | 10 mg/kg/week |
| 2 | 10 | 7.5 mg/kg q 14 days |
| 3 | 20 | 10 mg/kg/week |
| 4 | 20 | 7.5 mg/kg q 14 days |
| 5 | 30 | 10 mg/kg/week |
| 6 | 30 | 7.5 mg/kg q 14 days |
| 7 | 40 | 10 mg/kg/week |
| 8 | 40 | 7.5 mg/kg q 14 days |

Additional Indications

In addition to the treatment of non-small cell lung cancer, breast cancer, colorectal cancer, soft tissue or bone sarcomas and endometrial cancer, the mTOR inhibitor and anti-IGF-1R antibody combination may also be useful for the treatment of the following cancers: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, -malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma,; and Adrenal glands: neuroblastoma. Thus, the term "cancerous cell" as provided herein, includes a cell afflicted by any one of the above-identified conditions.

The mTOR inhibitor and anti-IGF-1R antibody combination of the invention may also be useful in treating the following disease states: keloids and psoriasis.

Further included within the scope of the invention is a method of treating or preventing a disease in which angiogenesis is implicated, which is comprised of administering to a mammal in need of such treatment a therapeutically effective amount of the combination of the present invention. Ocular neovascular diseases are an example of conditions where much of the resulting tissue damage can be attributed to aberrant infiltration of blood vessels in the eye (see WO 00/30651, published 2 Jun. 2000). The undesirable infiltration can be triggered by ischemic retinopathy, such as that resulting from diabetic retinopathy, retinopathy of prematurity, retinal vein occlusions, etc., or by degenerative diseases, such as the choroidal neovascularization observed in age-related macular degeneration Inhibiting the growth of blood vessels by administration of the present compounds would therefore prevent the infiltration of blood vessels and prevent or treat diseases where angiogenesis is implicated, such as ocular diseases like retinal vascularization, diabetic retinopathy, age-related macular degeneration, and the like.

Further included within the scope of the invention is a method of treating or preventing a non-malignant disease in which angiogenesis is implicated, including but not limited to: ocular diseases (such as, retinal vascularization, diabetic retinopathy and age-related macular degeneration), atherosclerosis, arthritis, psoriasis, obesity and Alzheimer's disease (Dredge et al., *Expert Opin. Biol. Ther*. (2002) 2(8):953-966). In another embodiment, a method of treating or preventing a disease in which angiogenesis is implicated includes: ocular diseases (such as, retinal vascularization, diabetic retinopathy and age-related macular degeneration), atherosclerosis, arthritis and psoriasis.

Further included within the scope of the invention is a method of treating hyperproliferative disorders such as restenosis, inflammation, autoimmune diseases and allergy/asthma.

Further included within the scope of the instant invention is the use of the instant combination to coat stents and therefore the use of the instant compounds on coated stents for the treatment and/or prevention of restenosis (WO03/032809).

Further included within the scope of the instant invention is the use of the instant combination for the treatment and/or prevention of osteoarthritis (WO03/035048).

Further included within the scope of the invention is a method of treating hypoinsulinism.

Exemplifying the invention is the use of the mTOR inhibitor and anti-IGF-1R antibody combination described above in the preparation of a medicament for the treatment and/or prevention of non-small cell lung cancer, breast cancer, colorectal cancer, soft tissue or bone sarcomas and endometrial cancer.

Additional Anti-Cancer Agents

The mTOR inhibitor and anti-IGF-1R antibody combination of the instant invention is also useful in combination with additional therapeutic, chemotherapeutic and anti-cancer agents. Further combinations of the mTOR inhibitor and anti-IGF-1R antibody combination of the instant invention with therapeutic, chemotherapeutic and anti-cancer agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such additional agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The mTOR inhibitor and anti-IGF-1R antibody combination of the instant invention may be particularly useful when co-administered with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycanninomycin, annamycin, galarubicin, elinafide, MEN 10755, 4-demethoxy-3-deamino-3-aziridinyl-4-methylsulphonyl-daunorubicin (see WO 00/50032), Raf kinase inhibitors (such as Bay43-9006) and additional mTOR inhibitors.

An example of a hypoxia activatable compound is tirapazamine.

Examples of proteosome inhibitors include but are not limited to lactacystin and MLN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl) benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797. In an embodiment the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNPI350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',': 6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and LNX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,1'-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-1), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589,485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-a, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (*PNAS*, Vol. 89, p. 7384 (1992); *JNCI*, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin, Orthop*. Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in U.S. Ser. Nos. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK11 and CHK12 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, Nature, 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Ala such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469), inhibitors of Raf kinase (for example BAY-43-9006), inhibitors of MEK (for example CI-1040 and PD-098059), inhibitors of mTOR (for example Wyeth CCl-779), and inhibitors of PI3K (for example LY294002).

As described above, the combinations with NSAID's are directed to the use of NSAID's which are potent COX-2 inhibiting agents. For purposes of this specification an NSAID is potent if it possesses an $IC_{50}$ for the inhibition of COX-2 of 1 µM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. Nos. 5,474,995, 5,861,419, 6,001,843, 6,020,343, 5,409,944, 5,436,265, 5,536,752, 5,550,142, 5,604,260, 5,698,584, 5,710,140, WO 94/15932, U.S. Pat. Nos. 5,344,991, 5,134, 142, 5,380,738, 5,393,790, 5,466,823, 5,633,272 and 5,932, 598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pridinyl)pyridine; or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof.

Other examples of angiogenesis inhibitors include, but are not limited to, endostatin, ukrain, ranpirnase, IM862, 5-methoxy-4-∂2-methyl-3-(3-methyl-2-butenypoxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RP14610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the αvβ5 integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl]indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9, 10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, ST1571A, N-4-chlorophenyl-4-(4-pyridylmethyl)-1-phthalazinamine, and EMD121974.

Combinations with compounds other than anti-cancer compounds are also encompassed in the instant methods. For example, combinations of the mTOR inhibitor and anti-IGF-1R antibody combination of the instant invention with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Ophthalmol. Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitnzone), fenofibrate, gemfibrozil, clofibrate, GW2570, SB219994, AR-H039242, JTT-501, MCC-555, GW2331, GW409544, NN2344, KRP297, NP0110, DRF4158, NN622, 01262570, PM3182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy) phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (*Am. J. Hum. Genet.* 61:785-789, 1997) and Kufe et al (*Cancer Medicine,* 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, 0C144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

The mTOR inhibitor and anti-IGF-1R antibody combination of the instant invention may also be administered with an agent useful in the treatment of anemia. Such an anemia treatment agent is, for example, a continuous eythropoiesis receptor activator (such as epoetin alfa).

The mTOR inhibitor and anti-IGF-1R antibody combination of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

The mTOR inhibitor and anti-IGF-1R antibody combination of the instant invention may also be administered with an immunologic-enhancing drug, such as levamisole, isoprinosine and Zadaxin.

The mTOR inhibitor and anti-IGF-1R antibody combination of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

The mTOR inhibitor and anti-IGF-1R antibody combination of the instant invention may also be useful for treating or preventing breast cancer in combination with aromatase inhibitors. Examples of aromatase inhibitors include but are not limited to: anastrozole, letrozole and exemestane.

The mTOR inhibitor and anti-IGF-1R antibody combination of the instant invention may also be useful for treating or preventing cancer in combination with siRNA therapeutics.

The mTOR inhibitor and anti-IGF-1R antibody combination of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

The mTOR inhibitor and anti-IGF-1R antibody combination of the instant invention may also be useful for treating or preventing cancer in combination with inhibitors of Akt. Such inhibitors include compounds described in, but not limited to, the following publications: WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469.

The mTOR inhibitor and anti-IGF-1R antibody combination of the instant invention may also be useful for treating or preventing cancer in combination with PARP inhibitors.

Radiation therapy itself means an ordinary method in the field of treatment of cancer. For radiation therapy, employable are various radiations such as X-ray, γ-ray, neutron ray, electron beam, proton beam; and radiation sources. In a most popular radiation therapy, a linear accelerator is used for irradiation with external radiations, γ-ray.

The mTOR inhibitor and anti-IGF-1R antibody combination of the instant invention may also be useful for treating cancer in further combination with the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elsparg); azacitidine (Vidaza®); bevacuzimab (Avastin®); bexarotene capsules (Targretin®); bexarotene gel (Targretin®); bleomycin (Blenoxane®); bottezomib (Velcade®; busulfan intravenous (Busulfex®); busulfan oral (Mylleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); B Solution (Elliott's B Solution®); epirubicin (Ellence®); Epoetin alfa (Epogen®); erlotinib (Tarceva®); estramustirie (Emcyt®); etoposide phosphate (Etopophos®); etoposide, VP-16 (Vepeside); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gerntuzumab ozogamicin (Mylotarg®); goserelin acetate (Zoladex Implant®); goserelin acetate (Zoladex®); histrelin acetate (Histrelin Implant®); hydroxyurea (Hydreag); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®), leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofiin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/1-131 tositumomab (Bexxar®); Trastuzumab (Herceptin®); tretinoin, ATRA (Vesanoid®); Uracil Mustard (Uracil Mustard Capsules®); valrubicin (Valstare); vinblastine (Velban®); vincristine (Oncovin®); vinorelbine (Navelbine®); and zoledronate (Zometa®).

All patents, publications and pending patent applications identified are hereby incorporated by reference.

The abbreviations used herein have the following tabulated meanings. Abbreviations not tabulated below have their meanings as commonly used unless specifically stated otherwise.

| | |
|---|---|
| Cu(OAc)$_2$ | copper acetate |
| DIPEA | diisopropylethylamine |
| EDC | 1-ethyl-3-(3-dimethylaminopropyl) carbodiimide hydrochloride |
| HOBt | N-hydroxybenzotriazole |
| NH$_4$Cl | ammonium chloride |

The mTOR inhibitors and anti-IGF-1R antibodies of the instant invention can be prepared according to the following general schemes, using appropriate materials, and are further exemplified by the subsequent specific examples. The specific anticancer agents illustrated in the examples are not, however, to be construed as forming the only genus that is considered as the invention. The illustrative Examples below, therefore, are not limited by the anticancer agents listed or by any particular substituents employed for illustrative purposes. Those skilled in the art will readily understand that known variations of the conditions and processes of the following preparative procedures can be used to prepare these compounds. All temperatures are degrees Celsius unless otherwise noted.

METHODS OF SYNTHESIS

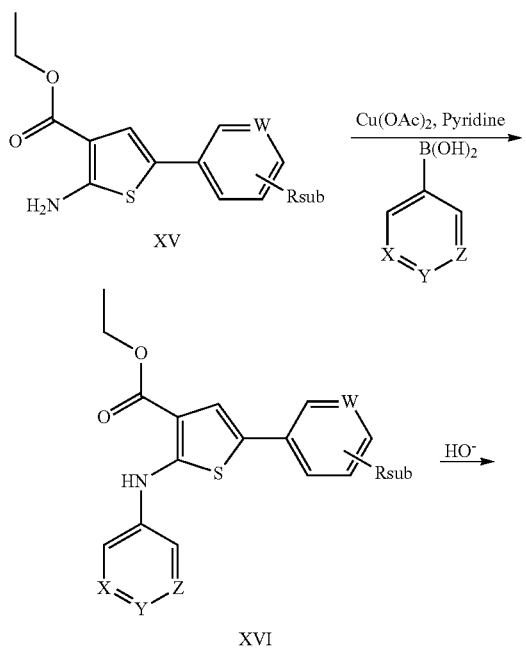

SCHEME 1

31

-continued

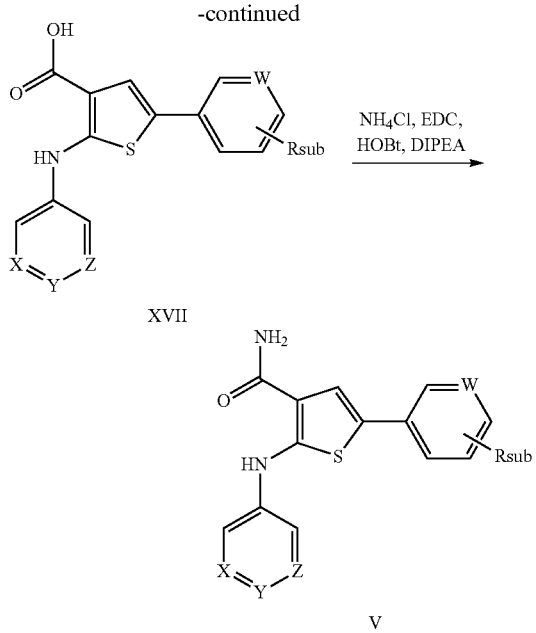

XVII

V

The invention will now be illustrated in the following non-limiting examples in which, unless otherwise stated:
1. All final products were analyzed by NMR, LCMS.
2. Intermediates were analyzed by NMR and/or TLC and/or LCMS.
3. Most compounds were purified by flash chromatography on silica gel, reverse phase HPLC, recrystallization, and/or swish (suspension in a solvent followed by filtration of the solid).
4. The course of the reactions was followed by thin layer chromatography (TLC) and/or LCMS and reaction times are given for illustration only.

EXAMPLE 1

Dimethyl-Phosphinic Acid C-43 Rapamycin Ester

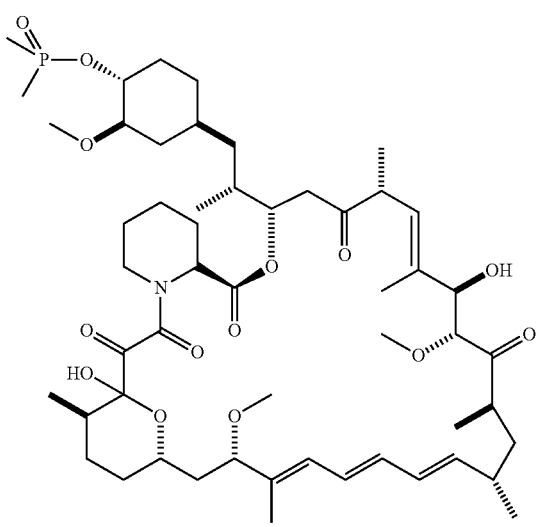

To a cooled (0° C.) solution of rapamycin (0.1 g, 0.109 mmol) in 1.8 mL of dichloromethane was added 0.168 g (0.82 mmol)

32 of 2,6-di-t-butyl-4-methylpyridine, under a stream of $N_2$, followed immediately by a solution of dimethylphosphinic chloride (0.062 g, 0.547 mmol) in 0.2 mL of dichloromethane. The slightly yellow reaction solution was stirred at 0° C., under an atmosphere of $N_2$, for 3.5 h (reaction monitored by TLC). The cold (0° C.) reaction solution was diluted with ~20 mL EtOAc then transferred to a separatory funnel containing EtOAc (150 mL) and saturated $NaHCO_3$ (100 mL). Upon removing the aqueous layer, the organic layer was washed successively with ice cold 1N HCl (1×100 mL), saturated $NaHCO_3$ (1×100 mL), and brine (1×100 mL), then dried over $MgSO_4$ and concentrated. The crude product was purified by silica gel flash chromatography (eluted with 1:10:3:3 MeOH/DCM/EtOAc/hexane) to provide 0.092 g of a white solid: $^1H$ NMR (300 MHz, $CDCl_3$) δ4.18 (m, 1H), 4.10 (m, 1H), 3.05 (m, 1H), 1.51 (m, 6H); $^{31}P$ NMR (121 MHz, $CDCl_3$) δ 53.6; 1013 m/z (M+Na).

EXAMPLE 2

Dimethyl-Phosphinic Acid C-43 Rapamycin Ester, Alternative Synthesis

Rapamycin and dichloromethane are charged into a nitrogen-purged reaction flask. The stirred solution is cooled to approximately 0° C. (an external temperature of −5±5° C. is maintained throughout the reaction). A solution of dimethylphosphinic chloride (2.0 molar equivalents) in dichloromethane is then added over a period of approximately 8-13 minutes. This is followed immediately by the addition of a solution of 3,5-lutidine (2.2 molar equivalents) in dichloromethane over a period of approximately 15-20 minutes. Throughout both additions, the internal temperature of the reaction sssstays below 0° C. The cooled reaction solution is stirred for 1 hour and then transferred, while still cold, to an extractor containing saturated aqueous $NaHCO_3$ and methyl-t-butyl ether (MTBE), ethyl acetate or diethyl ether. In-process samples are removed at 30 and 60 minute time points. Samples are prepared in a similar fashion to that described for the reaction workup. Reaction progress is monitored by TLC (1:10:3:3 MeOH/DCM/EtOAc/hexanes) and reverse-phase HPLC analyses. The isolated organic layer is successively washed with ice cold 1N HCl, saturated aqueous $NaHCO_3$ (2×), saturated aqueous NaCl, and dried over sodium sulfate. Upon filtration and solvent removal, the residue undergoes solvent exchange with acetone followed by concentration in vacuo to provide crude product, which may be analyzed for purity by normal- and reversed-phase HPLC.

EXAMPLE 3

Generation and Selection of the Murine Monoclonal Antibody (MAb)

With the aim of generating MAb specifically directed against IGF-IR and not recognizing the IR, a protocol comprising 6 screening stages was envisaged.
It consisted in:
  immunizing mice with recombinant IGF-IR, in order to generate hybridomas,
    screening the culture supernatants by ELISA on the recombinant protein which served for immunization,
    testing all the supernatants of hybridomas positive by ELISA on the native receptor overexpressed on the surface of MCF-7 tumor cells,
    evaluating the supernatants of hybridomas positive in the two first screenings in terms of differential recognition of IGF-IR and of IR on insect cells infected with baculoviruses respectively expressing IGF-IR or IR, verifying that the antibodies selected at this stage were capable of inhibiting in vitro the induced IGF1 proliferation of the MCF-7 cells, ensuring the in vivo activity, in nude mice, of the candidate retained in terms of impact on the growth of the tumor MCF-7.

All of these different stages and results obtained will be briefly described below in example 1.

Figure 3A:
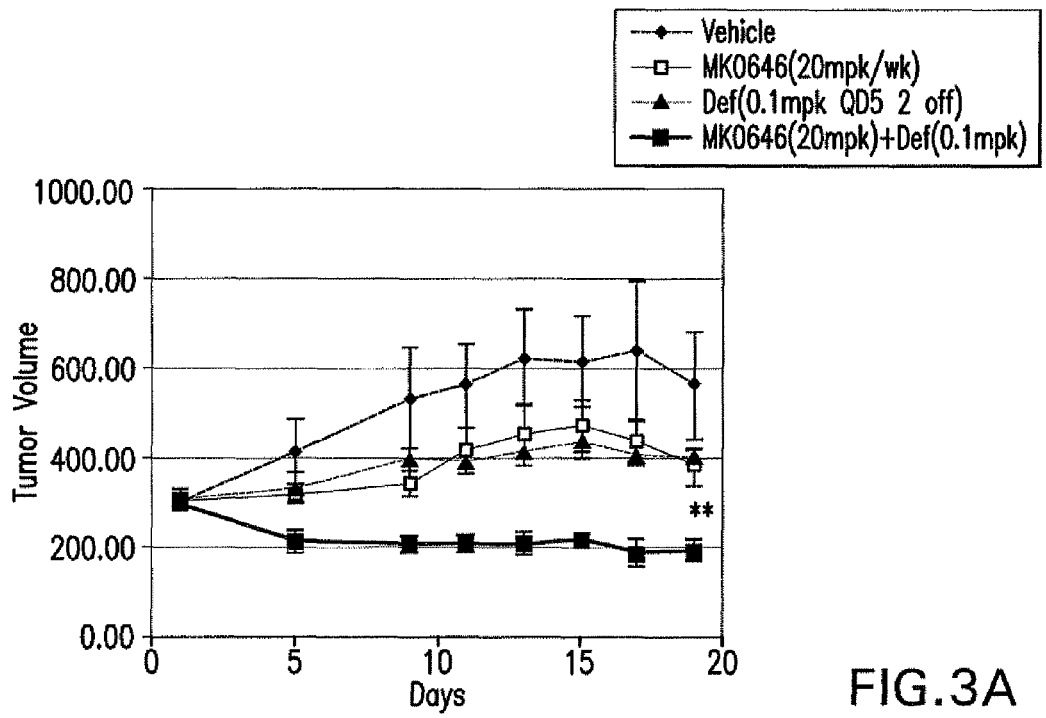
FIG. 3: Anti-tumor activity of Ridaforolimus & MK-0646 combinations in mutant-KRAS xenograft tumors. Combined treatment with MK-0646 & Ridaforolimus is efficacious in blocking the A549 xenograft growth. Significant tumor growth inhibition was observed in the combination treatment groups at multiple concentrations of MK-0646 & Ridaforolimus combination as evaluated by 2 way ANOVA analysis.
Figure 3B:
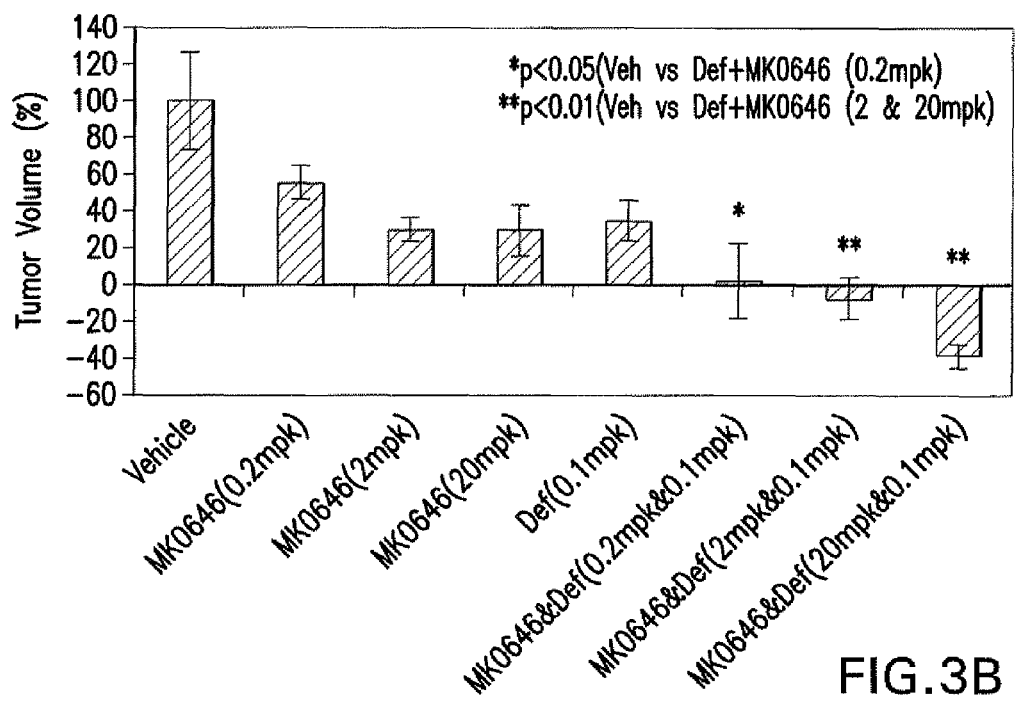

For the immunization stage, mice were injected twice, by the subcutaneous route, with 8 µg of recombinant IGF-IR. Three days before the fusion of the cells of the female rat with the cells of the murine myeloma Sp2OAg14, the mice were stimulated by an intravenous injection of 3 µg of the recombinant receptor. Fourteen days after the fusion, the supernatants of hybridomas were screened by ELISA, on plates sensitized by recombinant IGF-IR. The hybridomas whose supernatants were found positive were conserved and amplified before being tested on the FACS can so as to verify that the antibodies produced were likewise capable of recognizing native IGF-IR. In order to do this, MCF-7 cells from an estrogen-dependent tumor of the breast overexpressing IGF-IR were incubated with each of the culture supernatants produced by the hybridomas selected in ELISA. The native/MAb receptor complexes on the surface of the cell were revealed by a secondary anti-species antibody coupled to a fluorochrome. FIGS. 3A to 3C show a histogram type obtained with the supernatant of the hybridoma 7C10 (FIG. 3C) compared with a cell labeling alone+secondary antibody (FIG. 3A) or with a labeling utilizing a control isotype (FIG. 3B).

At this stage of the selection, only the hybridomas secreting MAb at the same time recognizing the recombinant receptor and the native receptor were selected and cloned. The MAb secreted by these hybridomas were produced and then purified before being tested on the FACScan, according to the method described above, on SD insect cells expressing IGF-IR or IR in order to eliminate the hybridomas at the same time recognizing the two receptors. FIG. 4A shows a total recovery of the histograms 1, 2, 3 respectively corresponding to the noninfected cells+secondary antibodies (1), to the noninfected cells labeled by αIR3+secondary antibodies (2) and to the noninfected cells labeled by an anti-IR antibody+secondary antibodies (3). This first result shows well the absence of IGF-IR and of IR detectable on the surface of these noninfected insect cells. FIG. 4B shows a labeling of infected cells by a baculovirus expressing IGF-IR. In this second figure, the αIR3, used as a positive control, labels well, as expected, the cells (peak 2), while the anti-IR (peak 3) is superimposed on the peak of single cells. Finally, in FIG. 4C, it is shown that the anti-IR labels well, as expected, the Sf9 cells expressing the IR (peak 3), but in an unexpected manner, the αIR3 described in the literature as specific for IGF-IR seems likewise to recognize the IR (peak 2).

The results obtained in this third screening system are summarized in table 1 and show the generation of an MAb: 7C10, satisfying the criteria of recognition of the IGF-IR and of nonrecognition of the IR. The isotyping of the Mab 7C 10 has shown that it involves an IgG1.

TABLE 1

Comparative reactivity of MAb 7C10 on Sf9 insect cells expressing IGF-IR or IR

| | MFI (Mean fluorescence intensity) | | |
|---|---|---|---|
| | Noninfected cells | IGF1R + cells | IR + cells |
| Cells | 8 | 8 | 7 |
| Anti-IR | 4.6 | 9 | 91 |
| Anti-IGF-IR (αIR3) | 9 | 35 | 32 |
| EC2 | 8 | 13 | 11 |
| Anti-mouse FITC | 4.3 | 9 | 13 |
| UltraCulture medium | 9 | 10 | 11 |
| 15B9 | 7.5 | 25 | 77.8 |
| 9F5D | 8 | 41 | 40 |
| 13G5 | 7.8 | 37 | 24 |
| 7C10 | 8.6 | 49 | 13 |

The two last screenings provided for the selection of the MAb consisted in verifying that the latter was very capable of inhibiting the cell proliferation induced by the IGF-I in vitro and in vivo on the cell line MCF-7.

Figure 5:
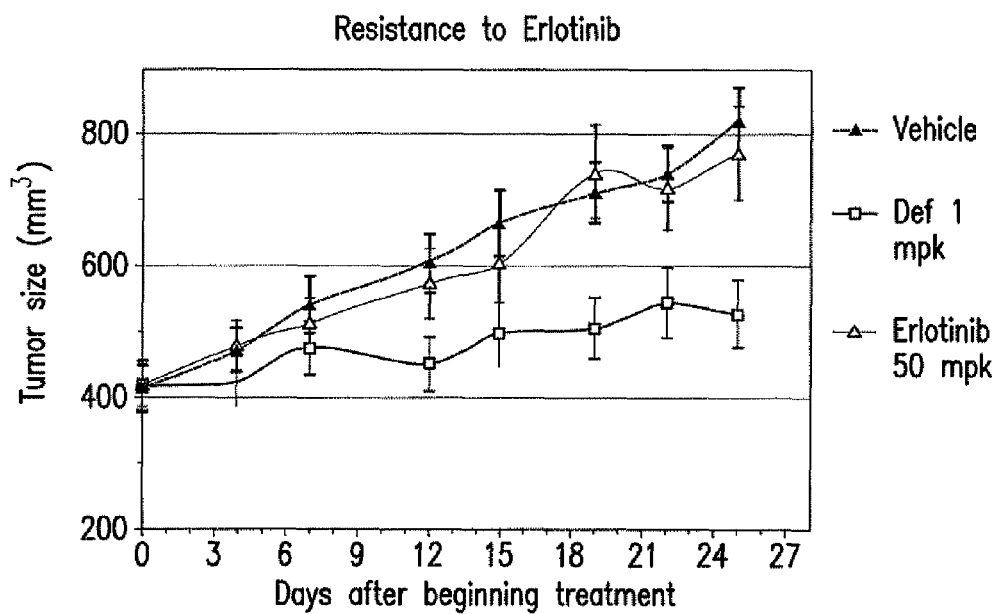
FIG. 5: A549 xenograft model is resistant to Erlotinib treatment. No significant growth inhibition was observed in Erlotinib treated group as compared to vehicle.

For the in vitro selection, the MCF-7 cells were inoculated, deprived of fetal calf serum, then incubated in the presence of increasing concentrations of IGF-I (from 1 to 50 ng/ml) in the presence or in the absence of the 7C10 antibody to be tested added to a final concentration of 10 µg/ml. In this experiment, the commercial αIR3MAb was introduced as a positive control and the 7G3 MAb (isolated in parallel to the 7C10 and weakly recognizing the native receptor (MFI on the FACS of 50 compared with 200 for the MAb 7C10)) as a control isotype. The cell proliferation is estimated by following on the 13 counter the incorporation of tritiated thymidine by the cells. The results are expressed as a proliferative index. The data presented in FIG. 5 show that IGF 1 is capable of stimulating in a dose-dependent manner the proliferation of the MCF-7 cells. The MAb αIR3, used as a positive control, completely inhibits the proliferation of the MCF-7 cells induced by the IGF-I. In the same manner, the MAb 7C10 significantly inhibits the growth of the MCF-7 cells induced by IGF-I. Finally, the MAb 703 used as an isotype control turns out well, as expected, without effect on the tumor cell growth in vitro of the MCF-7 cell.

The in vivo selection was carried out in an established tumor model. In order to do this, nude mice received a subcutaneous implant of slow-release estrogen, indispensable for the taking of the tumor in a murine model. Twenty-four hours after implantation of the estrogens, $5.10^6$ MCF-7 cells are grafted onto the right flank of the mouse subcutaneously. Five days after this cell graft, the tumors are measurable and batches of 6 mice are formed at random. The treatment of the mice is carried out twice per week, during 5 to 6 weeks, at the dose of 250 µg/dose/mouse. In the control group, the mice are treated in the same fashion with a murine control isotype. The results presented in FIG. 6A show a very significant inhibition of the tumor growth induced by the antibody 7C10. This activity is particularly unexpected if reference is made to the data available concerning αIR3, always used as a reference in the domain of the receptor for IGF1, and known for not having any activity in vivo on the growth of estrogen-dependent tumors (see FIG. 6B). In the same way, compared with the results obtained with the recombinant antibody scFv-Fc derived from the murine MAb 1H7 (see FIG. 6C), the MAb 7C 10 is much more efficacious in the in vivo inhibition of the growth of the MCF-7 cells.

EXAMPLE 4

Effect of MK-0646 and Ridaforolimus in Human Lung Cancer Cell Line

Summary: Rationale for the proposed combination is predicated on observations suggesting that each of MK-0646 and Ridaforolimus, when combined, act by inhibiting oncogenic signaling through the PI3 Kinase signaling pathway and that the two in combination produce more effective pathway inhibition than either agent acting alone. See also (Cao et al Cancer Research 2008).

Briefly, each of MK-0646, a monoclonal antibody targeting IGF1R and mTOR inhibitor, a rapamycin analogue, Ridaforolimus is currently being developed for the treatment of lung cancer. Treatment with rapamycin analogues results in the up-regulation of AKT signaling as measured by phosphorylation of AKT. While inhibition of mTOR by Ridaforolimus can induce tumor growth arrest, it abrogates a negative feedback loop mediated by IRS-1, resulting in activation of AKT, which has been implicated in reducing its anti-tumor activity. This feedback activation of AKT is mediated via the IGF signaling pathway. A recent clinical study suggests that activation of AKT via this feedback mechanism may be associated with a shorter time-to-progression in patients treated with rapamycin (Cloughesy et al PLoS Medicine, 2008). In addition mTOR appears to be a key enhancer of MK-0646 efficacy thus blocking this feedback activation of AKT by combining ridaforolimus with MK-0646 may be beneficial for inhibiting the PI3K pathway as well as enhancing anti-tumor activity of MK0646. The rationale for the proposed combination is predicated, in part, on the above observation. To investigate this possibility, the inventors examined the proposed combination in a panel of lung cancer cell lines. Detailed here below is data supporting the hypothesis that the combination treatment comprising MK-0646 and Ridaforolimus significantly enhanced PI3K pathway inhibition and cell proliferation. As well, the proposed combination demonstrated enhanced anti-tumor activity in an erlotinib-resistant, KRAS-mutant lung cancer xenograft model.

(A) MK-0646+Ridaforolimus Combination Enhances PI3K Pathway Targeting:

Methods: All the NSCLC cell lines were obtained from ATCC and maintained in RPMI 1640 with 10% fetal bovine serum (Invitrogen). For western blot analysis total protein lysates from cells cultured in 6 well plates and treated with either Ridaforolimus (10 nM) or MK-0646 (10 ng/ml) or in combination for 4 hrs and harvested in SDS gel loading dye (Invitrogen). Samples were western blotted with indicated total or phosphospecific antibodies followed by a secondary antibody (Cell Signaling Technology, CST) and then incubated with SuperSignal chemiluminescence substrate (Pierce). The blots were then exposed to a Kodak Biomax Light Film. The antibodies against ERK, p-ERK (Thr202/Tyr204), AKT and p-AKT (Ser473), IGF S6K & P-S6K (T389), IRS1 & P-IRS1 (S302) and actin were obtained from CST. Cell cycle analysis was performed in H2122 cells following 24 hr treatment with indicated compounds (see above). One million cells were permiabilized and stained with propidium Iodide (PI) as described by the manufacturer (BD Pharmingen #550825). PI binds to both DNA and RNA, so the latter was removed by digestion with ribonucleases (RNase A). The content of DNA as determined by flow cytometry, can reveal useful information about the cell cycle. Cells in G2 and M phases of the cell cycle have double the DNA content of those in G0 and G1 phases. Cells in S phase have a DNA content lying between these extremes. PI is detected in the orange range of the spectrum using a 562-588 nm band pass filter using a flow cytometer.

Figure 1B:
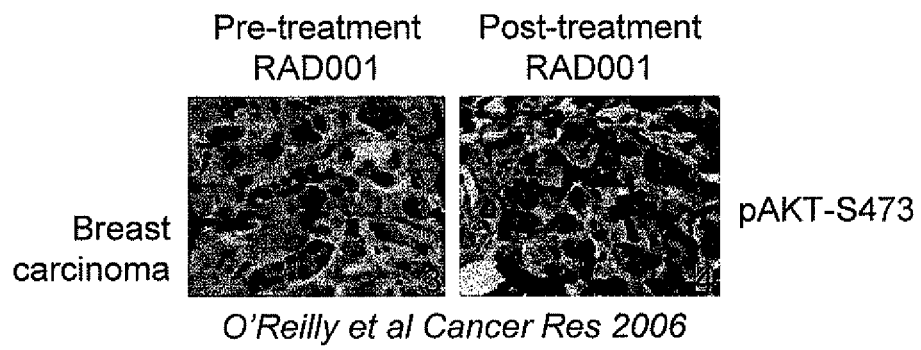
Figure 1C:
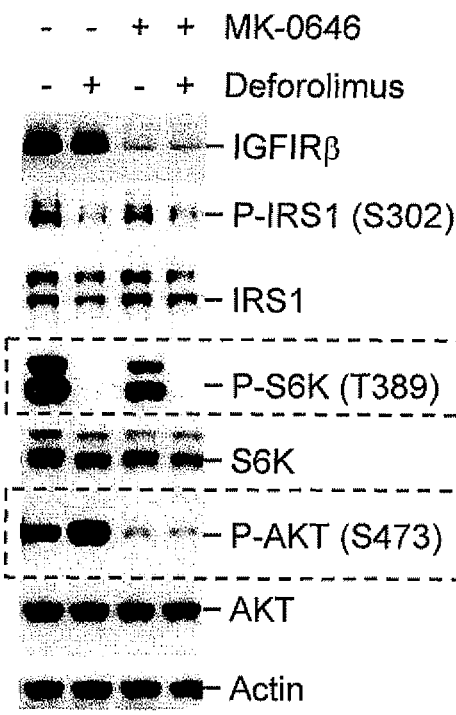
Figure 1D:
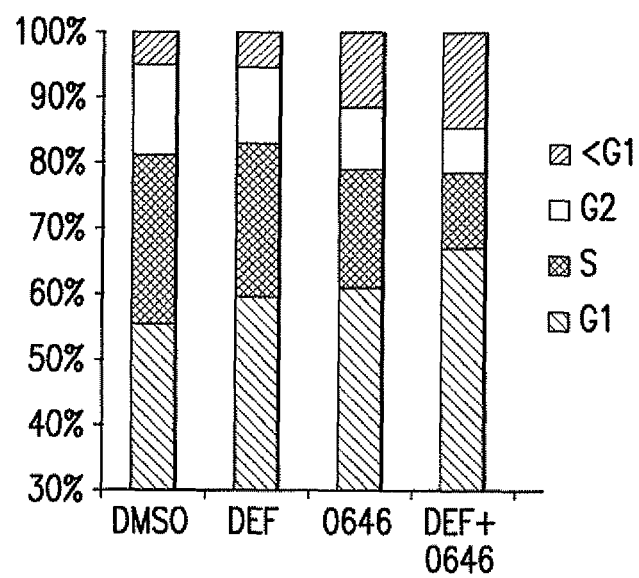

Analysis: The combination of Ridaforolimus and MK-0646 has been evaluated in human lung cancer cell lines. Both compounds act by inhibiting oncogenic signaling through the PI3 Kinase signaling pathway. Studies performed here confirmed other reports that the two agents produce more effective pathway inhibition than either agent alone. It has been previously reported that the inhibition of mTOR (TORC1 complex) leads to a secondary effect that results in elevation of the active, phosphorylated form of AKT which promotes tumor cell survival. Importantly, inhibition of IGF1R by MK-0646 is effective in blocking this effect. FIG. 1 illustrates the feedback loop phenomena, showing that combining the two agents counters this effect and improves the targeting of oncogenic PI3K signaling. mTOR inhibitors are effective inhibitors of S6 Kinase and thus protein translation. However, the inhibition of S6 kinase also leads to the abrogation of a negative feedback loop mediated by S6 kinase (S6K) which suppresses IGF1R signaling. The effect of blocking this feedback loop is that IGF1R signaling is elevated, leading to increased levels of the active, phosphorylated form of AKT (AKT-P), which drives tumor survival. Treatment of patients with the rapalogue RAD001, which is similar to ridaforolimus, results in elevated AKT-P(O'Reilly, K. E. et al, Cancer Research, 2006; FIG. 1B). Some investigators have suggested that this may limit the effectiveness of the compound when used as single agent in certain contexts (Cloughesy et al PLoS Medicine, 2008). Since this effect is thought to depend on IGF1R activity, the inventors proposed using an mTOR inhibitor in combination with MK-0646, an inhibitor of IGF1R. To date, the data collected is in accord with prior findings. The data suggest that co-treatment of the non-small cell lung cancer cell line H2122 with the combination of the Ridaforolimus and MK-0646 was more effective in blocking signaling than either agent alone (FIG. 1C, right), preventing both phosphorylation of S6K (by Ridaforolimus) and AKT phosphorylation (by MK-0646). The combination is also more effect than the single agents at inhibiting cell cycle and survival of these tumor cells in vitro. Treatment of the H2122 tumor cell line with the combination led to a decrease in the percentage of actively dividing cells and an increase in dead or dying cells (FIG. 1D).

(B) Ridaforolimus+MK-0646 Combination Increases In Vitro Efficacy.

Figure 2A:
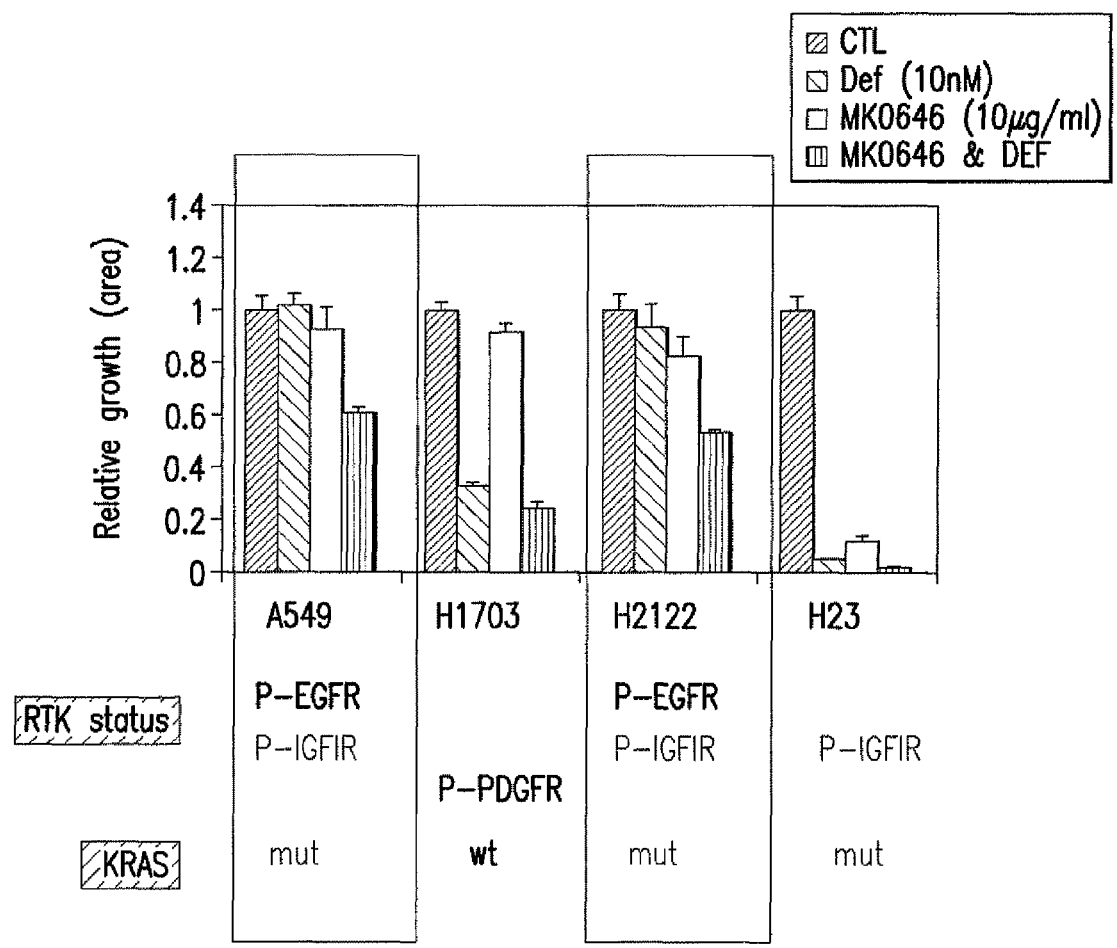
FIG. 2: Ridaforolimus & MK-0646 combination increases efficacy in vitro. Lung cancer cell lines were cultured in soft-agar in the presence of MK-0646 or ridaforolimus or the combination. Soft agar colony formation was quantified using a fluorescent dye (LavaCell) and colony area and number were enumerated using an image acquisition and analysis platform (Isocyte). A) The relative colony area in the well of a 96 well plate is plotted. The combination significantly enhanced growth inhibition (P<0.02) in A549 & H2122 cell lines. The activation status of RTKs as measured by P-RTK array and the activating mutations in KRAS are indicated below. B) The relative soft agar colony formation in response to either Ridaforolimus (10 nM) or MK-0646 (10 ug/ml) or the combination in 9 NSCLC cell lines is plotted. The cell lines were divided based on the activating mutations in KRAS.
Figure 2B:
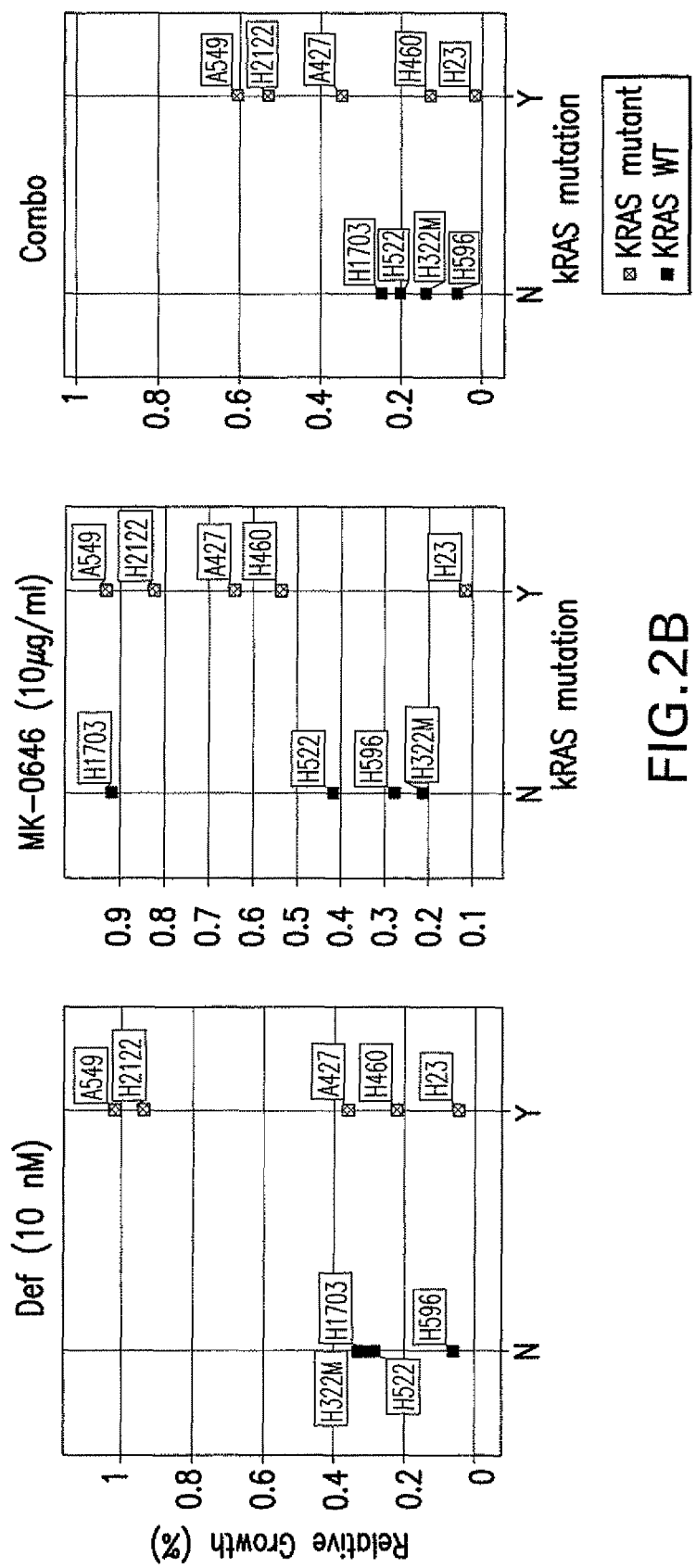

To assess the efficacy of MK-0646 or ridaforolimus or the combination the inventors evaluated anchorage-independent growth in presence of these inhibitors in a panel of lung tumor cell lines using a soft agar assay. The colony formation assay was performed in the absence of supplemented IGF. The effect of MK-0646 or ridaforolimus or the combination was assessed in 9 cell lines (5 mutant-KRAS; 4 wt-KRAS). MK-0646 single agent sensitivity was observed in a KRAS mutant cell line (1123) and 3 KRAS wildtype cell lines (FIG. 2). H1703 with low expression of IGF1R was resistant to MK-0646. In two KRAS mutant cell lines (A549 & H2122) with high levels of IGF1R, there was only limited single agent activity while the combination showed significant growth inhibition. Overall most cell lines in the panel showed a combination benefit. No significant correlation of KRAS-status and response to the combination was observed.

Methods: Soft agar assays were conducted in 96 well glass bottom plates (MatriCal). Cells were seeded at a concentration of 3,000-9,000 cells per well in 100 μl RMPI 1640 supplemented with 14% FBS and 0.3% (w/v) SeaPlaque Agarose (Lonza Rockland, Inc) on top of a bottom layer of consisting of the same culture media supplemented with 0.8% agarose. Compounds were added in 100 μl of culture media supplemented after agarose had solidified. Cells were incubated for 7-14 days before staining overnight with LavaCell (Active Motif). Colonies were quantified using an Isocyte™ laser scanning cytometer. The ability of MK-0646 to inhibit anchorage independent growth alone or in combination with standard of care agents was evaluated in a soft agar colony forming assay. The RTK status was evaluated in total protein lysates using the P-RTK arrays (R&D biosciences) as described by the manufacturer. The activating mutations in KRAS were identified from published cancer genome data bases (Sanger).

(C) Combined Benefit of MK-0646 and Ridaforolimus in Combination A549 Lung Xenograft Model.

Figure 4:
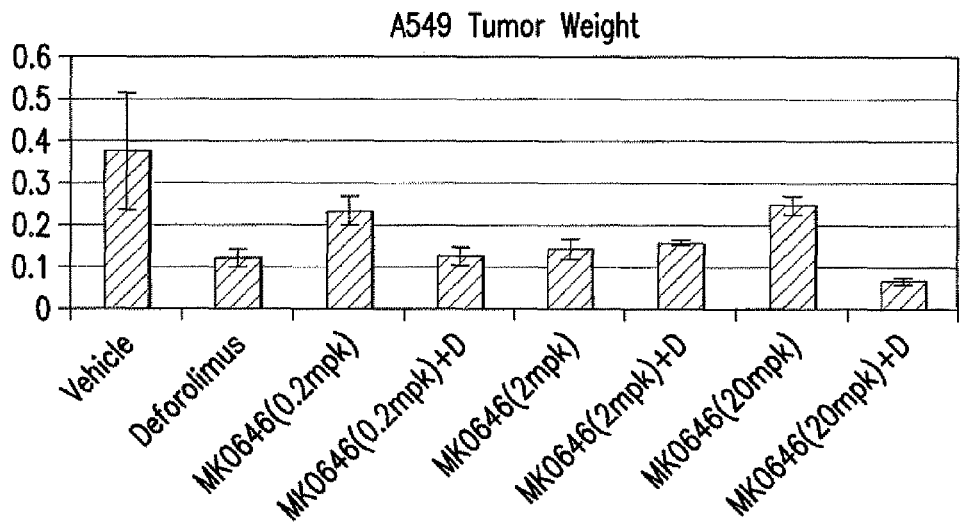
FIG. 4: Tumor weight is statistically reduced with high concentrations of MX-0646 in combination with Ridaforolimus. Mice were dosed with MK-0646 (20 mpk) either alone or in combination with Ridaforolimus (0.1 mpk) for 3 weeks. Tumor weights (see above) were statistically smaller at the higher doses of MK-0646 in combination with Ridaforolimus highlighting the regression of the tumors.

The combination of Ridaforolimus and MK-0646 was evaluated in the A549 mutant-KRAS xenograft model. The combination displayed significant anti-tumor activity when MK-0646 is dosed at either 0.2 or 2 mpk in combination with ridaforolimus (0.1 mpk). However, dosing MK-0646 at 20 mpk in combination with ridaforolimus (0.1 mpk) shows tumor regression with statistical significance over either agent alone (FIG. 3). Similar results are observed when comparing tumor weights across the groups. There is a statistically significant decrease in tumor weight in mice that were dosed with MK-0646 (20 mpk) in combination with Ridaforolimus (0.1 mpk) over either agent alone (FIG. 3). Together, these data provide strong in vivo evidence that lower doses of MK-0646 in combination with Ridaforolimus induces tumor stasis while higher doses of MK-0646 (20 mpk) in combination with Ridaforolimus can cause tumor regression. Also significant reduction in tumor weight was observed at this combination (FIG. 4). Treatment with Erlotinib in this model did not result in any appreciable tumor growth inhibition (FIG. 5). In this model the lack of efficacy with Erlotinib is not surprising given the activating mutation in KRAS present in this model. As a consequence, the data demonstrates a combination benefit to MK-0646 & Ridaforolimus in an erlotinib refractory NSCLC model.

Method: $2.5 \times 10^6$ A549 human NSCLC cells were injected subcutaneously into the right flank of 4-6 week old athymic Nude-Foxn1nu mice (Charles River Laboratories). When tumors reached a size of ~300 mm3 (Length*Width*Width*0.5), mice were randomized into treatment groups. Mice (n=8/group) were dosed with vehicle once per week for 3 weeks (qwk×3) (20 mM L-Histidine, 150 mM NaCl, 0.5% PS80 pH=6) or 0.2 or 2 or 20 mpk of MK-0646 intra-peritoneal mg/kg MK-0646 qwk×3 or Ridaforolimus (0.1 mg/kg) or in combination with MK-0646 for 3 weeks. Animals were weighed and tumor volumes were determined by calipering 2 times per week during the study and at termination. Tumor weight was determined at termination. On day 21 Animals were sacrificed by $CO_2$ asphyxiation. Mice were sacrificed 24 hr after the final dose. At time of sacrifice, the tissue samples were collected and processed.

The relative tumor volumes at the end of the treatment are depicted in the table below. The negative values represent tumor regression. Significant tumor growth inhibition was observed in all MK-0646 & Ridaforolimus combination groups as compared to single agents.

TABLE 2

Tumor growth inhibition by MK-0646 in combination with Ridaforlolimus.

| Samples | Relative tumor growth (%) |
|---|---|
| Control (Vehicle) | 100.00 |
| MK0646(0.2mpk) | 55.29 |
| MK0646(2mpk) | 30.09 |
| Mk0646(20mpk) | 29.30 |
| Rida(0.1mpk) | 35.01 |
| MK0646&Rida(0.2mpk& 0.1mpk) | 1.55* |
| MK0646&Rida(2mpk& 0.1mpk) | −7.85** |
| MK0646&Rida(20mpk&0.1mpk) | −39.58** |

*P < 0.05;
**P < 0.01

EXAMPLE 5

MK-0646 Enhancer Screen

Summary: Multiple lines of evidence suggest that hyperactivation of IGF 1 R signaling correlates with tumor progression. Both IGF1R and its ligand IGF1 are frequently overexpressed in human cancers and are associated with poor prognosis (Miller and Yee, 2005). Furthermore, forced overexpression of either IGF1 or IGF in animal tissues leads to spontaneous tumor formation (Jones et al, 2006). In contrast, decreased IGF IR function may prevent tumorigenesis as fibroblasts isolated from IGF1R knockout mice are resistant to transformation by overexpression of oncogenes (Sell et al. 1994).

A lentivirus-mediated RNAi screen was used to ascertain whether an IGF-1R specific antibody (MK-0646) could be used to enhance effectiveness in a combination therapy protocol. As a consequence of the screen, 37 targets were identified, whose silencing significantly enhanced tumor cell sensitivity to MK-0646. Among these enhancers were shRNAs targeting 4 distinct positive regulators of the PI3 kinase signaling cascade (PI3KCA, PDPK1, AKT2, and FRAP1/mTOR). In contrast an shRNA targeting a negative regulator of the pathway, PTEN, conveyed resistance to MK-0646. Taken together, these data suggest that tumors negative for PTEN may exhibit resistance to MK-0646. More, the data support the hypothesis suggesting combining inhibitors targeting the PI3K pathway such as mTOR1 or AKT1 or PI3Ki with MK-0646 may indeed potentiate MK-0646 response.

Results: The inventors applied lentivirus-mediated RNAi screening to identify kinase regulators of tumor cell sensitivity to an insulin-like growth factor 1 receptor (IGF1R) mab, specifically MK-0646. Towards this end, 1439 lentiviral shRNA vectors targeting 480 distinct humankinases were screened to identify potential enhancers of the anti-tumor cell activity of MK0646.

Nine distinct screens with various concentrations of MK-0646 (200 μg/ml to 300 ng/ml) were carried out using MK-0646 and the kinase-targeting lentiviral shRNA vectors. From the screens, a list of 37 consensus hits representing the top 3% of MK-0646 enhancers were identified. See FIG. 10. Prominent among these hits were shRNA vectors targeting multiple members of the canonical phosphatidyl inositol 3-kinase (PI3K) pathway-PIK3CA, via two distinct vectors, PDPK1, AKT2, and FRAP1/mTOR. Two separate consensus hits from the screen (CCRK and NEK8), had been previously been identified in siRNA screens as regulators of the PI3K/AKT pathway, See Brace et al. 2006. Also notable among the list of MK-0646 enhancers were shRNAs targeting two members of the Ras signaling cascade (B-Raf by two distinct vectors and MAP2K1 by two distinct vectors). In all, 11 of the top 37 shRNA hits targeted kinases that are members of two established signaling cascades hypothesized to be activated following IGF activation. See FIG. 6.

An independent proliferation assay based on colony formation with HT29 colon cancer cells was performed to corroborate the above referenced screening hits.

Figure 6:
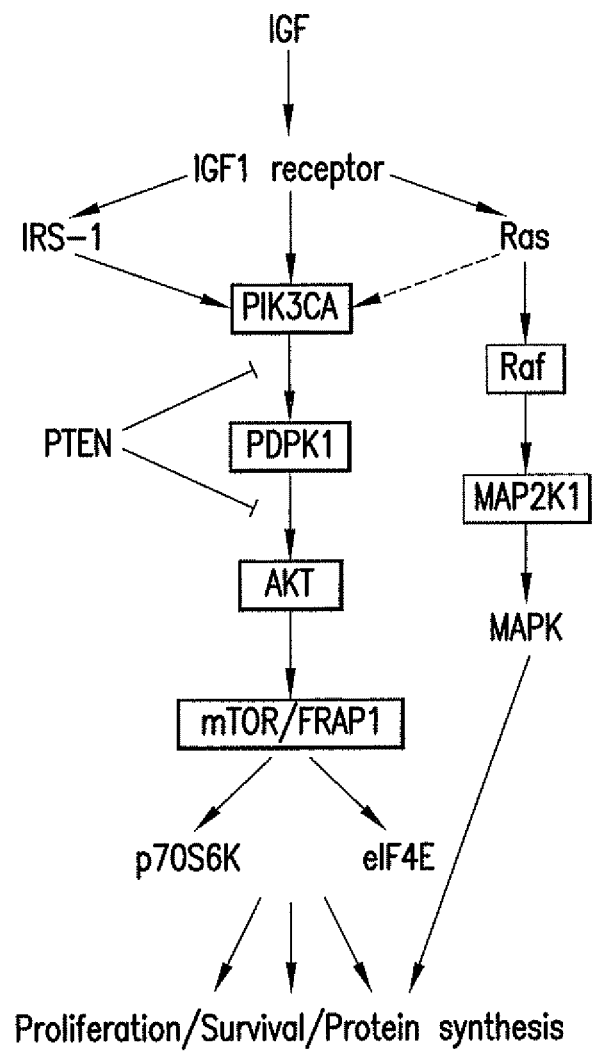
FIG. 6: IGF1 receptor signal transduction. Screening hits targeting the phosphatidyl-inositiol 3-kinase (PIK3CA) pathway and the Ras pathway are boxed in red or blue, respectively.

Method/Analysis—FIG. 6: Following infection with fresh vector, cells were exposed to a 5-dose titration of MK-0646 and then allowed to form colonies over the course of 9 days. The ability of each of the 37 shRNA hits to enhance sensitivity to MK-0646 was compared with an empty vector control as well as three randomly chosen "non-hit" shRNA vectors from the shRNA kinase vector set. In addition, because multiple positive effectors of the PI3K pathway scored as hits, a separate vector that efficiently silences the lipid phosphatase PTEN, the primary negative regulator of PI3K signaling was also tested. PTEN is a established tumor suppressor that acts by dephosphorylating the product of PI3K activity, thus preventing activation of downstream kinases. No vector (MK-0646 alone) and no treatment (no virus and no drug) controls were also performed.

Methods: The lentiviruses targeting 480 individual genes, mostly kinases, were generated by packaging 1439 lentiviral shRNA vectors (Kalypsis library, GNF) in 293T cells by co-transfecting with packaging vectors as recommended by invitrogen lentiviral packaging system (Virapower packaging system, Invitrogen). HT-29 cells (n=500) were cultured in a 384 well plate in presence of 10% FBS in DMEM. Next day cells were infected with 10 µl of packaged virus. On day 3 media was removed and cells were allowed to recover for a day. On day 4 cells were treated with MK0646 (200 µg/ml to 300 ng/ml). On day 8 amount of cell growth was assessed by staining with alamar blue as described previously (Klinghoffer et al 2008 Assay and Drug Development Technologies).

Figure 7A:
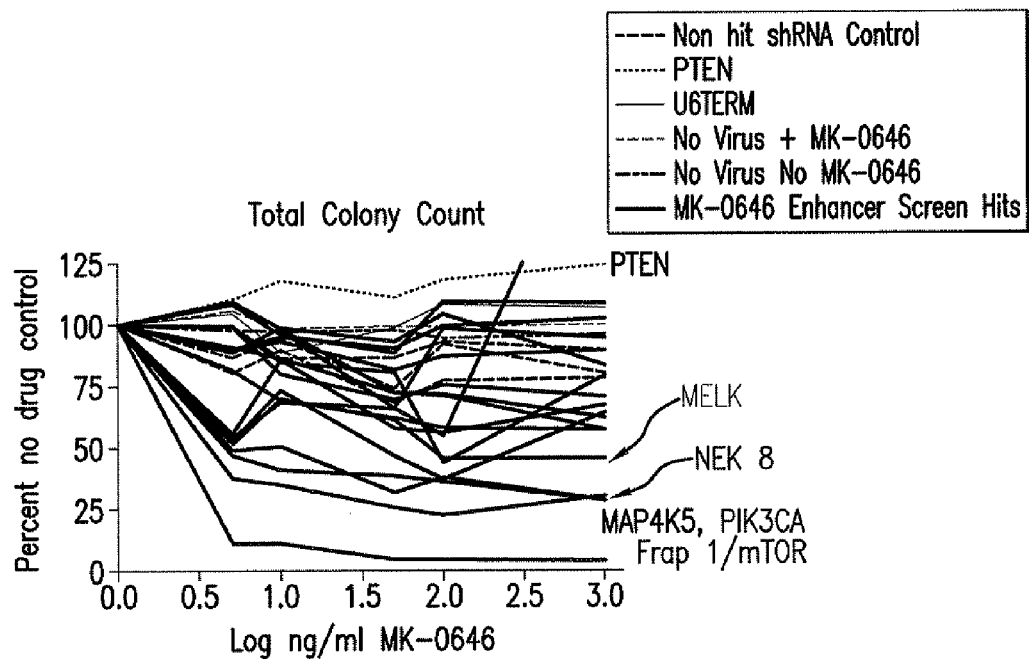
FIG. 7: Hit verification by colony assay demonstrates that shRNAs targeting PI3K pathway regulators strongly influence MK-0646 efficacy. Colony count (A) and colony area (B) were determined by scanning plates on an Alpha Imager. The top three strongest enhancers of MK-0646 were shRNAs that silenced effectors of the PI3K pathway (highlighted in red), whereas shRNA targeting PTEN conveyed resistance to drug.
Figure 7B:
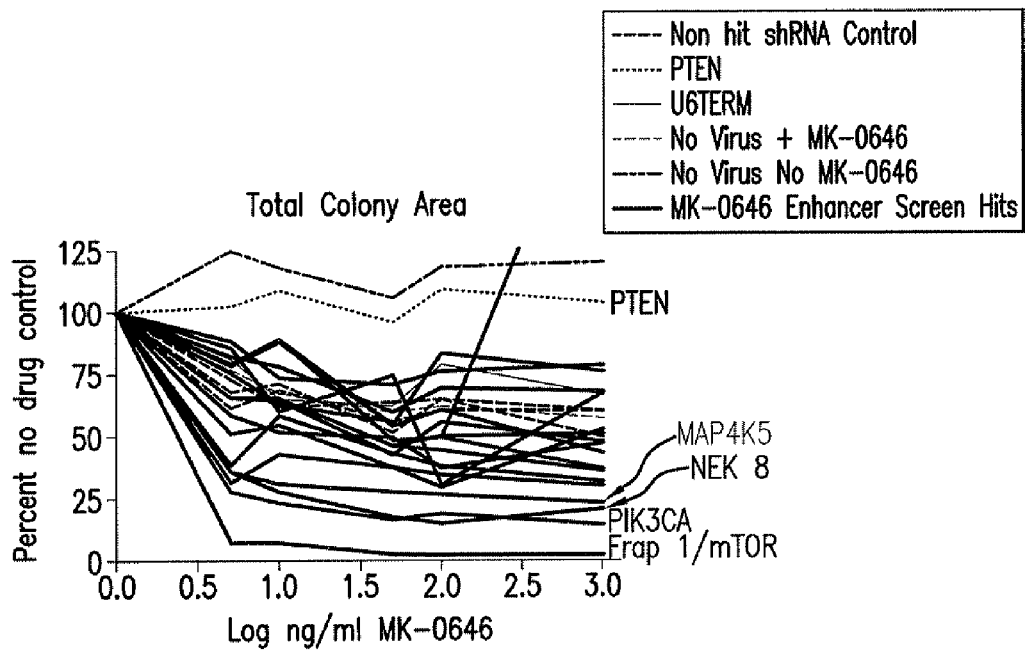

Method—FIG. 7: HT29 cells were seeded at 1500 cells/well in 6 well plates, and exposed to virus for 16 hr. Virus was removed and replaced with fresh medium containing no drug or a dilution of MK-0646 (0.05, 0.1, 0.5, 1, or 10 ug/ml). MK-0646 was replaced every 3 days over the course of the assay. Plates were stained with crystal violet on day 9 post drug addition. The colony number and area were calculated by imaging with Alpha Imager.

Comparison of the three randomly chosen shRNA vectors to empty vector and no vector controls showed no difference in tumor cell sensitivity to MK-0646. In contrast, 11 out of 20 screening hits that could be assessed in this assay resulted in two-fold or greater enhancement of MK-0646 inhibition of tumor cell proliferation. Refer to FIG. 7.

Quantitative real-time PCR analysis demonstrated that 10/11 of these vectors silenced their targets >50% and 7/11>70%, suggesting that the observed enhancement was due to the intended silencing—FIG. 10. As well, by use of this assay, 17 of the 37 shRNA hits resulted in cell toxicity in the absence of drug, preventing an assessment of MK-0646 sensitization. These toxic shRNAs were analyzed using a short-term (72 hr) Alamar blue assay similar to the primary screen except that cells were exposed to a 10-dose titration of MK-0646 following infection. As a consequence of this assay, additional 8 shRNAs were identified demonstrating significant (p<0.05) enhancement of tumor cell sensitivity to MK-0646. See FIG. 11.

Referring to FIGS. 7 and 10, consistent with a dominant role for PI3K pathway signaling in IGF-mediated tumor growth, the top three MK-0646 enhancers by colony assay were vectors targeting PI3K, FRAP1/mTOR, and NEK8 (these three vectors resulted in 86%, 80%, and 70% target silencing, respectively).

In addition, the strongest enhancer by 72-hr Alamar blue assay was a vector targeting the putative PI3K pathway regulator, CCRK (64% target silencing; not shown). Conversely cells exposed to vector targeting PTEN were resistant to the anti-proliferative effect of MK-0646, displaying growth similar to cells that were not treated (FIG. 6). Vectors targeting members of the Ras pathway, MAP2K1 and B-raf (97% and 75% silencing respectively), were also confirmed. See FIG. 10. Given that extensive cross-regulation exists between members of the PI3K and Ras signaling cascades, it is hypothesized that the sensitizing effect of MAP2K1 and B-raf shRNA is due, in part, to quenching of PI3K signaling.

To date, in cases where two shRNAs targeting the same gene demonstrated enhancement in the primary screen (P1K3CA, 13-raf, MAP2K1, BUB1, and CSNK1A1), one of the two shRNAs confirmed, while the other appeared to have demonstrated toxicity in the absence of drug. Validation of the second shRNA may require a shorter assay format.

To further support the PTEN result, the assay was performed on cells that harbored stable integration of the PTEN shRNA. Comparison of these to cells with stable expression of vector control, or shRNAs targeting CSK and MAP4K5 was initiated. Vectors targeting CSK and MAP4K5 were consensus hits from the primary screen but only MAP4K5 confirmed in the colony assay. Similar to the results in the application of fresh virus, the cell line expressing the PTEN shRNA demonstrated MK-0646 resistance by colony assay, whereas lines expressing the CSK shRNA responded in similar manner to vector control, and cells expressing the MAP4K5 shRNA were sensitized to drug. See FIG. 8.

Figure 8:
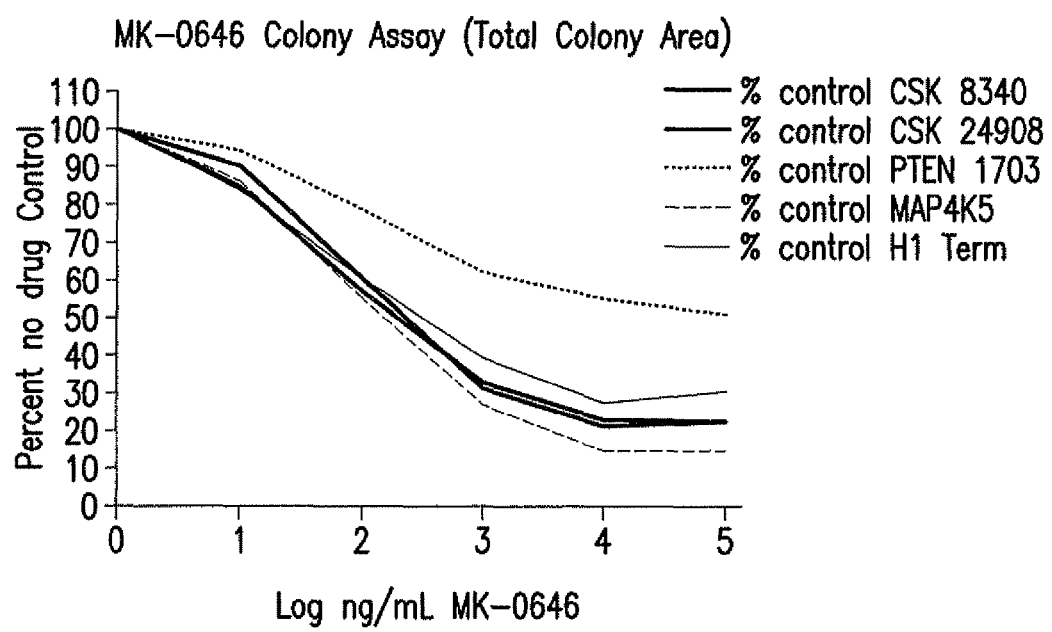
FIG. 8: Stable silencing of PTEN in HT29 colon cancer cells conveys resistance to MK-0646. Stable HT29 cells expressing various shRNAs targeting PTEN or CSK or MAP3K were generated and tested for sensitivity to MK-0646 in the colony formation assay. Silencing of PTEN showed reduced growth inhibition by MK-0646.

Method—FIG. 8: HT29 cells harboring stable integration shRNA targeting PTEN, CSK, and MAP4K5 were seeded at 1500 cells/well in 6 well plates. The next day cells were fed fresh medium containing no drug, or 0.01, 0.1, 1, 10, or 100 ug/ml MK-0646. MK-0646 was replaced every 3 days over the course of the assay. Plates were stained with crystal violet on day 9 post drug addition. Colony growth was quantified as described above. Responses to MK-064.6 were similar to what was observed following acute exposure to each lentiviral vector analyzed above.

The data and the attendant observations suggest that patients with tumors bearing loss-of-function mutations in PTEN may respond poorly to treatment with MK-0646. Because such mutations are common in cancer, the inventors in an attempt to determine whether MK-0646 resistant cells could be re-sensitized to drug by inhibiting PI3K peroemed additional assays.

Method—FIG. 9: HT29 cells with stable expression of vector control (red line), responsive to MK-0646, or with stable expression of PTEN shRNA (blue line), resistant to MK-0646, were infected with shRNA vectors targeting PI3K, PDPKI, or MELK. (A) Similar to our assay, shown in FIG. 6, infection of vector control HT29 cells with shRNA vectors targeting PI3K or MELK results in strong and moderate sensitization respectively to MK-0646, whereas shRNA targeting PDPKI has no effect. (B) Infection of stable PTEN shRNA HT29 cells with MELK or PDPK1 has no effect on reversing MK-0646 resistance caused by PTEN deficiency. In contrast, infection with the PI3K shRNA vector completely reverses this resistance.

Figure 9A:
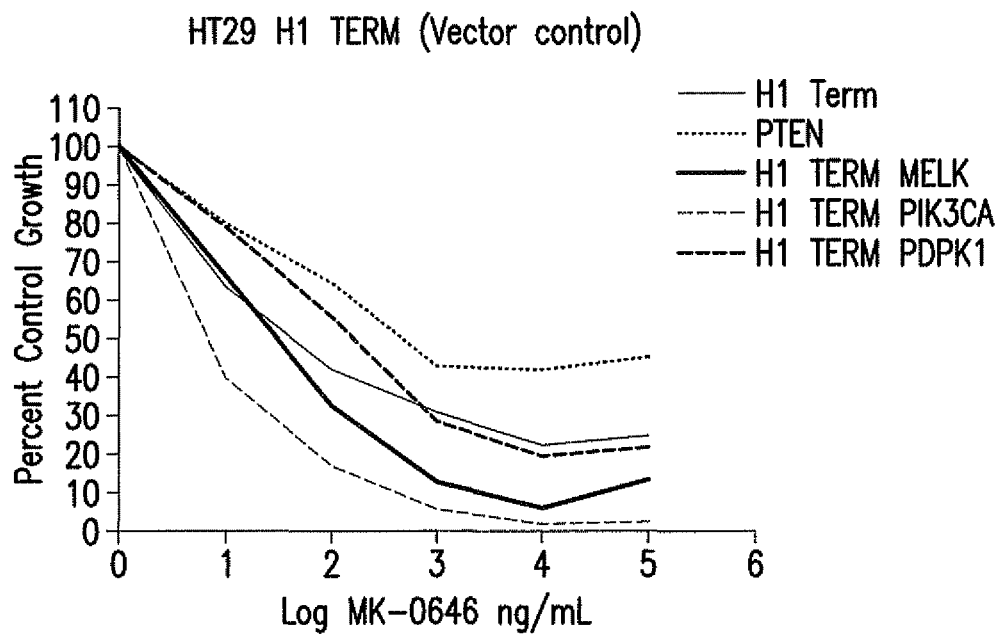
FIG. 9: Silencing of PI3K but not PDPK1 or MELK resensitizes PTEN-deficient HT29 cells to the effect of MK-0646. RNAi mediated knock-down of PTEN confers resistance to MK-0646 mediated growth inhibition (see FIGS. 7 & 8). The growth of PTEN-knockdown cells can be blocked by combined inhibition of IGF1R and PIK3CA by MK-0646 & PI3K RNAi.
Figure 9B:
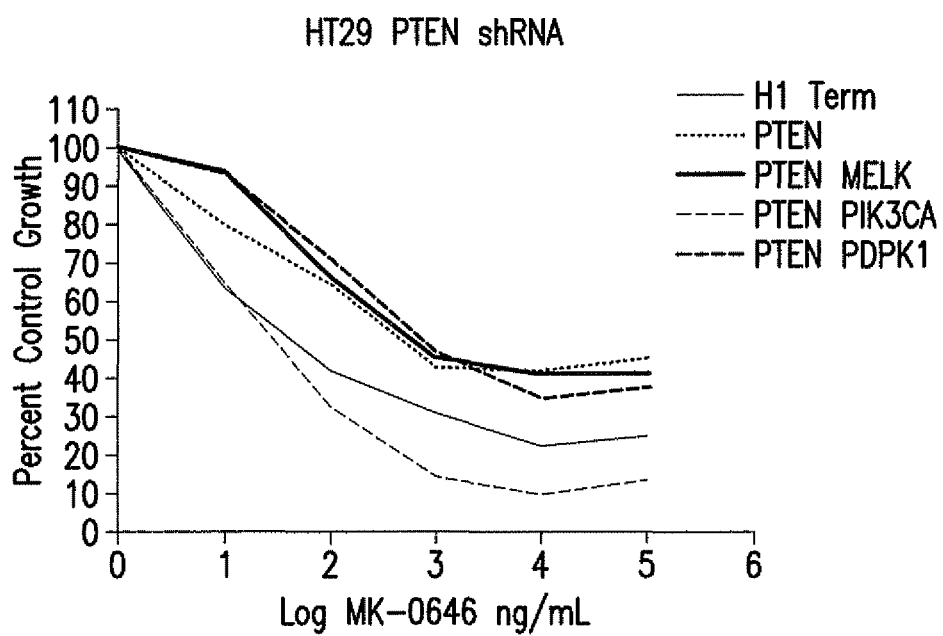
Figure 12:
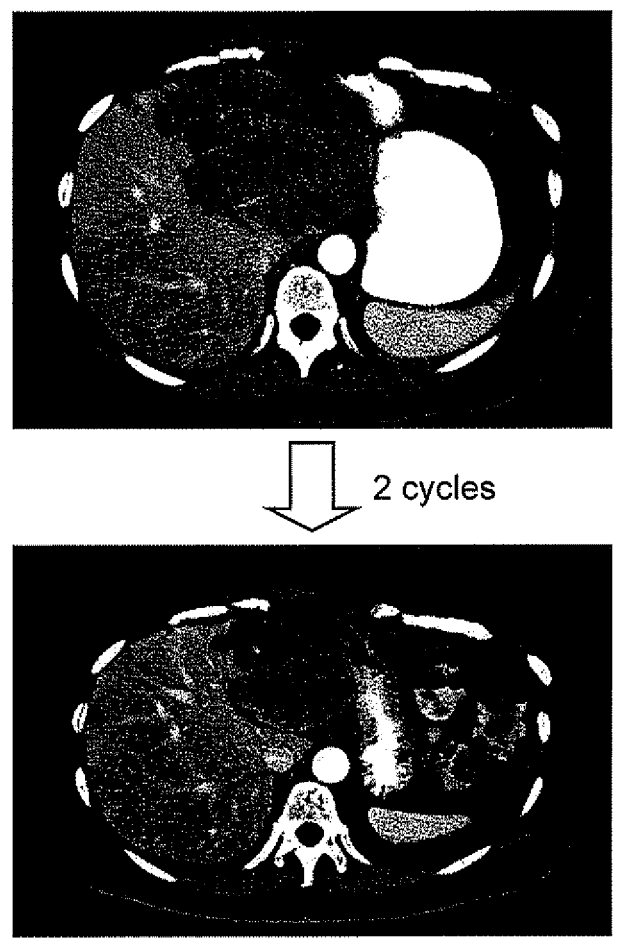
FIG. 12: CT images of a patient responding to the ridaforolimus-dalotuzumab combination. The images are from a 56 year old female with estrogen receptor positive breast cancer metastatic to the liver, as shown in the figure, and to other sites. The patient had progressed after multiple prior chemotherapies and hormonal therapies. The top panel shows a large tumor in the left lobe of the liver, and the bottom panel shows the same tumor, markedly reduced in size, following two cycles of treatment on a Phase 1 clinical trial of ridaforolimus combined with dalotuzumab. The patient achieved a partial response that was ongoing after more than 8 months of study therapy.

Analysis: Consistent with our previous results, cells expressing the PTEN shRNA were resistant to MK-0646 compared with cells expressing vector control. Referring to FIG. 9A, consistent with our previous experiments, infection of control cells with vectors targeting either PI3K or MELK, but not PDPK1, sensitized cells to MK-0646. In PTEN-deficient cells, infection with the MELK shRNA had no impact as these cells remained resistant to MK-0646. Infection with the shRNA targeting PI3K, however, was able to re-sensitize the PTEN shRNA line to the effect of MK-0646—FIG. 9B. Thus, it appears that signaling through PI3K to be rate limiting for IGF1R-mediated tumor cell proliferation. This observation suggests that, whereas patients with hyperactive PI3K signaling may be unresponsive to monotherapy with an anti-IGF1R agents, a combination therapy with inhibitors of PI3K pathway members such as mTOR may indeed be effective.

While a number of embodiments of this invention have been described, it is apparent that the basic examples may be altered to provide other embodiments, encompassed by the present invention. Therefore, it will be appreciated that the scope of this invention is to be defined by the appended claims rather than by the specific embodiments, which have been represented by way of example.

---

SEQUENCE LISTING

Arg Ser Ser Gln Ser Ile Val His Ser Asn Gly Asn
Thr Tyr Leu Gln-SEQ. ID. NO. 1

Lys Val Ser Asn Arg Leu Tyr-SEQ. ID. NO. 2

Phe Gln Gly Ser His Val Pro Trp Thr-SEQ. ID.
NO. 3

Gly Gly Tyr Leu Trp Asn-SEQ. ID. NO. 4

Tyr Ile Ser Tyr Asp Gly Thr Asn Asn Tyr Lys Pro
Ser Leu Lys Asp-SEQ. ID. NO. 5

Tyr Gly Arg Val Phe Phe Asp Tyr-SEQ. ID. NO. 6

Asp Val Val Met Thr Gln Ser Pro Leu Ser Leu Pro
Val Thr Pro Gly Glu Pro Ala Ser Ile Ser Cys Arg
Ser Ser Gln Ser Ile Val His Ser Asn Gly Asn Thr
Tyr Leu Gln Trp Tyr Leu Gln Lys Pro Gly Gln Ser
Pro Gln Leu Leu Ile Tyr Lys Val Ser Asn Arg Leu
Tyr Gly Val Pro Asp Arg Phe Ser Gly Ser Gly Ser
Gly Thr Asp Phe Thr Leu Lys Ile Ser Arg Val Glu
Ala Glu Asp Val Gly Val Tyr Tyr Cys Phe Gln Gly
Ser His Val Pro Trp Thr Phe Gly Gln Gly Thr Lys
Val Glu Ile Lys-SEQ. ID. NO. 7

Asp Ile Val Met Thr Gln Ser Pro Leu Ser Leu Pro
Val Thr Pro Gly Glu Pro Ala Ser Ile Ser Cys Arg
Ser Ser Gln Ser Ile Val His Ser Asn Gly Asn Thr
Tyr Leu Gln Trp Tyr Leu Gln Lys Pro Gly Gln Ser
Pro Gln Leu Leu Ile Tyr Lys Val Ser Asn Arg Leu
Tyr Gly Val Pro Asp Arg Phe Ser Gly Ser Gly Ser
Gly Thr Asp Phe Thr Leu Lys Ile Ser Arg Val Glu
Ala Glu Asp Val Gly Val Tyr Tyr Cys Phe Gln Gly
Ser His Val Pro Trp Thr Phe Gly Gln Gly Thr Lys
Val Glu Ile Lys-SEQ. ID. NO. 8

Gln Val Gln Leu Gln Glu Ser Gly Pro Gly Leu Val
Lys Pro Ser Glu Thr Leu Ser Leu Thr Cys Thr Val
Ser Gly Tyr Ser Ile Thr Gly Gly Tyr Leu Trp Asn
Trp Ile Arg Gln Pro Pro Gly Lys Gly Leu Glu Trp
Met Gly Tyr Ile Ser Tyr Asp Gly Thr Asn Asn Tyr
Lys Pro Ser Leu Lys Asp Arg Ile Thr Ile Ser Arg
Asp Thr Ser Lys Asn Gln Phe Ser Leu Lys Leu Ser
Ser Val Thr Ala Ala Asp Thr Ala Val Tyr Tyr Cys
Ala Arg Tyr Gly Arg Val Phe Phe Asp Tyr Trp Gly
Gln Gly Thr Leu Val Thr Val Ser Ser-SEQ. ID.
NO. 9

Gln Val Gln Leu Gln Glu Ser Gly Pro Gly Leu Val
Lys Pro Ser Glu Thr Leu Ser Leu Thr Cys Thr Val
Ser Gly Tyr Ser Ile Thr Gly Gly Tyr Leu Trp Asn
Trp Ile Arg Gln Pro Pro Gly Lys Gly Leu Glu Trp
Ile Gly Tyr Ile Ser Tyr Asp Gly Thr Asn Asn Tyr
Lys Pro Ser Leu Lys Asp Arg Val Thr Ile Ser Arg
Asp Thr Ser Lys Asn Gln Phe Ser Leu Lys Leu Ser
Ser Val Thr Ala Ala Asp Thr Ala Val Tyr Tyr Cys
Ala Arg Tyr Gly Arg Val Phe Phe Asp Tyr Trp Gly
Gln Gly Thr Leu Val Thr Val Ser Ser-SEQ. ID.
NO. 10

Gln Val Gln Leu Gln Glu Ser Gly Pro Gly Leu Val
Lys Pro Ser Glu Thr Leu Ser Leu Thr Cys Thr Val
Ser Gly Tyr Ser Ile Ser Gly Gly Tyr Leu Trp Asn
Trp Ile Arg Gln Pro Pro Gly Lys Gly Leu Glu Trp
Ile Gly Tyr Ile Ser Tyr Asp Gly Thr Asn Asn Tyr
Lys Pro Ser Leu Lys Asp Arg Val Thr Ile Ser Val
Asp Thr Ser Lys Asn Gln Phe Ser Leu Lys Leu Ser
Ser Val Thr Ala Ala Asp Thr Ala Val Tyr Tyr Cys
Ala Arg Tyr Gly Arg Val Phe Phe Asp Tyr Trp Gly
Gln Gly Thr Leu Val Thr Val Ser Ser-SEQ. ID.
NO. 11

Asp Val Leu Met Thr Gln Ile Pro Leu Ser Leu Pro
Val Ser Leu Gly Asp Gln Ala Ser Ile Ser Cys Arg
Ser Ser Gln Ser Ile Val His Ser Asn Gly Asn Thr
Tyr Leu Gln Trp Tyr Leu Gln Lys Pro Gly Gln Ser
Pro Lys Leu Leu Ile Tyr Lys Val Ser Asn Arg Leu
Tyr Gly Val Pro Asp Arg Phe Ser Gly Ser Gly Ser
Gly Thr Asp Phe Thr Leu Lys Ile Ser Arg Val Glu
Ala Glu Asp Leu Gly Val Tyr Tyr Cys Phe Gln Gly
Ser His Val Pro Trp Thr Phe Gly Gly Gly Thr Lys
Leu Glu Ile Lys-SEQ. ID. NO. 12

Asp Val Gln Leu Gln Glu Ser Gly Pro Gly Leu Val
Lys Pro Ser Gln Ser Leu Ser Leu Thr Cys Ser Val
Thr Gly Tyr Ser Ile Thr Gly Gly Tyr Leu Trp Asn
Trp Ile Arg Gln Phe Pro Gly Asn Lys Leu Glu Trp
Met Gly Tyr Ile Ser Tyr Asp Gly Thr Asn Asn Tyr
Lys Pro Ser Leu Lys Asp Arg Ile Ser Ile Thr Arg
Asp Thr Ser Lys Asn Gln Phe Phe Leu Lys Leu Asn
Ser Val Thr Asn Glu Asp Thr Ala Thr Tyr Tyr Cys
Ala Arg Tyr Gly Arg Val Phe Phe Asp Tyr Trp Gly
Gln Gly Thr Thr Leu Thr Val Ser Ser-SEQ. ID.
NO. 13

---

What is claimed is:

1. A method of treating breast cancer with an mTOR inhibitor and an anti-IGF-1R antibody, wherein the mTOR inhibitor is ridaforolimus and the anti-IGF-1R antibody comprises a light chain comprising the amino acid sequence SEQ ID NO: 8 and a heavy chain comprising the amino acid sequence of SEQ ID NO: 10, wherein the ridaforolimus is orally administered at a dose of 10 mg or 20 mg per day five days a week and the antibody is administered intravenously at a dose of 10 mg/kg either once a week or once every other week.

* * * * *